(12) United States Patent
Taniguchi et al.

(10) Patent No.: US 8,729,195 B2
(45) Date of Patent: May 20, 2014

(54) ORGANOSILICON COMPOUND, METHOD FOR PRODUCING THEREOF, AND CURABLE SILICONE COMPOSITION CONTAINING THE SAME

(75) Inventors: Yoshinori Taniguchi, Ichihara (JP); Toyohiko Fujisawa, Ichihara (JP); Yasushi Sugiura, Ichihara (JP)

(73) Assignee: Dow Corning Toray Co., Ltd., Chiyoda-Ku, Tokyo (JP)

( * ) Notice: Subject to any disclaimer, the term of this patent is extended or adjusted under 35 U.S.C. 154(b) by 0 days.

(21) Appl. No.: 13/519,066

(22) PCT Filed: Dec. 20, 2010

(86) PCT No.: PCT/JP2010/073651
§ 371 (c)(1),
(2), (4) Date: Aug. 24, 2012

(87) PCT Pub. No.: WO2011/081165
PCT Pub. Date: Jul. 7, 2011

(65) Prior Publication Data
US 2012/0309921 A1    Dec. 6, 2012

(30) Foreign Application Priority Data

Dec. 28, 2009 (JP) .................. 2009-298549
Dec. 28, 2009 (JP) .................. 2009-298662
Dec. 28, 2009 (JP) .................. 2009-298663

(51) Int. Cl.
    *C08L 83/04*    (2006.01)
(52) U.S. Cl.
    USPC .................. 525/478; 528/15; 528/27; 528/31
(58) Field of Classification Search
    None
    See application file for complete search history.

(56) References Cited

U.S. PATENT DOCUMENTS

| | | | |
|---|---|---|---|
| 6,500,976 B2 | 12/2002 | Matsuda et al. | |
| 7,452,571 B2 * | 11/2008 | Tabei et al. | 427/301 |
| 8,314,200 B2 * | 11/2012 | Jandke et al. | 528/15 |
| 2002/0087019 A1 | 7/2002 | Matsuda et al. | |
| 2009/0274845 A1 | 11/2009 | Aketa et al. | |

FOREIGN PATENT DOCUMENTS

| | | | |
|---|---|---|---|
| CN | 1329640 | * | 2/2002 |
| CN | 101090922 | * | 12/2007 |
| EP | 0114636 A2 | | 8/1984 |
| JP | 59-137493 A | | 8/1984 |
| JP | 05-086075 | * | 4/1993 |
| JP | H05-086071 A | | 4/1993 |
| JP | H05-331291 A | | 12/1993 |
| JP | 07-126272 A | | 5/1995 |
| JP | 08-239391 | * | 9/1996 |
| JP | 2000-044583 | * | 2/2000 |
| JP | 2005-327777 A | | 11/2005 |
| JP | 2006-335857 | * | 12/2006 |
| JP | 2008-169386 A | | 7/2008 |

OTHER PUBLICATIONS

Machine-generated translation of JP 2006-335857 into the English language (Dec. 2006).*
English language abstract of JP 2006-335857 (Dec. 2006).*
Journal of Organometallic Chemistry (1975) 101, 187-203.*
English language abstract and translation for EP 0114636 extracted from the espacenet.com database on Aug. 22, 2012, 15 pages.
English language abstract and translation for JP 07-126272 extracted from the PAJ database on Aug. 22, 2012, 90 pages.
English language abstract not available for JP 59-137493; however, see equivalent EP 0114636. Original document extracted from the espacenet.com database, 6 pages.
English language abstract and translation for JP 2005-327777 extracted from the PAJ database on Aug. 22, 2012, 33 pages.
English language abstract for JP 2008-169386 extracted from the espacenet.com database on Aug. 22, 2012, 15 pages.
International Search Report for Application No. PCT/JP2010/073651 dated Mar. 22, 2011, 3 pages.
English language abstract and machine-assisted English translation for JP H05-086071 extracted from the PAJ database on Dec. 12, 2013, 23 pages.
English language abstract and machine-assisted English translation for JP H05-331291 extracted from the PAJ database on Jan. 22, 2014, 38 pages.

* cited by examiner

*Primary Examiner* — Marc Zimmer
(74) *Attorney, Agent, or Firm* — Howard & Howard Attorneys PLLC

(57) ABSTRACT

An objective of the present invention is to provide a curable silicone composition of the present invention exhibiting superior adhesive properties with respect to a poor-adhesive resin such as PPS, even if the composition is cured at a relatively low temperature for a short period. The aforementioned objective of the present invention is achieved by a curable silicone composition comprising: (A) an organopolysiloxane having at least two alkenyl groups in a molecule, (B) an organopolysiloxane having at least two silicon-bonded hydrogen atoms in a molecule, (C) a hydrosilylation-reaction catalyst, and (D) an acid anhydride having an alkoxy group bonding to a silicon atom or an alkoxyalkoxy group bonding to a silicon atom.

11 Claims, No Drawings

ORGANOSILICON COMPOUND, METHOD FOR PRODUCING THEREOF, AND CURABLE SILICONE COMPOSITION CONTAINING THE SAME

TECHNICAL FIELD

The present invention relates to a novel organosilicon compound, a method for producing thereof, and a curable silicone composition containing the same as an adhesion promoter.

This application is the National Stage of International Patent Application No. PCT/JP2010/073651, filed on Dec. 20, 2010, which claims priority to and all the advantages of Japanese Patent Application Nos. 2009-298549, 2009-298662, and 2009-298663, each filed on Dec. 28, 2009, the contents of which are incorporated herein by reference.

BACKGROUND ART

Patent Document 1 discloses a curable silicone composition which comprises a liquid or solid organopolysiloxane having at least two alkenyl groups in a molecule, wherein the liquid organopolysiloxane has a viscosity of 10 mPa·s or more at 25° C.; an organohydrogenpolysiloxane having at least two silicon-bonded hydrogen atoms and/or organohydrogensilane having at least two silicon-bonded hydrogen atoms in a molecule, wherein the organohydrogenpolysiloxane has a viscosity of 1,000 mPa·s or less at 25° C.; a hydrosilylation-reaction catalyst; a silicon compound having an epoxy group and at least one group selected from the group consisting of silicon-bonded hydrogen atoms, organoxysilyl groups and silicon-bonded alkenyl groups; and a liquid acid anhydride. In addition, Patent Document 2 discloses a curable silicone composition which comprises a diorganopolysiloxane having at least two alkenyl groups in a molecule; a three-dimensional organopolysiloxane resin containing at least one branch-formable unit selected from tri-functional siloxane units and tetra-functional siloxane units; an organohydrogenpolysiloxane having at least two silicon-bonded hydrogen atoms in a molecule; a hydrosilylation-reaction catalyst; an organosilicon compound as an adhesion promoter; and an acid anhydride which is liquid at room temperature.

However, even in the aforementioned curable silicone compositions, in the case of curing the compositions at a relatively low temperature, sufficient adhesive properties cannot be exhibited with respect to a poor-adhesive resin such as PPS, and there is a problem of insufficient adhesive strength.

On the other hand, Patent Documents 3 and 4 disclose a succinic anhydride-functional organosilicon compound as an organosilicon compound, and a method for producing the succinic anhydride-functional organosilicon compound characterized by a hydrosilylation reaction between a hydrogenalkoxysilane such as a trimethoxysilane; and a succinic anhydride having an unsaturated bond at the terminal of the molecular chain such as an allyl succinic anhydride or the like in the presence of a transition metal catalyst.

However, neither Patent Document 3 nor 4 discloses a succinic anhydride-functional organosilicon compound having a siloxane chain.

Furthermore, since the expensive transition metal catalyst and allyl succinic anhydride are used as industrial raw materials in the aforementioned method, there is a problem of an increase in the manufacturing cost of the target succinic anhydride-functional organosilicon compound. In addition, since it is generally difficult to handle a Si—H containing alkoxysilane such as trimethoxysilane, methylhydrogendimethoxysilane and the like as a raw material, it is necessary to introduce a new manufacturing facility or to improve the existing manufacturing facility. This is because the Si—H containing alkoxysilane easily disproportionates. For example, trimethoxysilane may disproportionate to form a mixture of tetrahydrogensilane and dimethoxydihydrogensilane in long term storage. Since organosilicon compounds having many Si—H bonds in one molecule generally exhibit spontaneous ignition, careful handling of such organosilicon compounds is required.

Patent Document 1: Japanese Unexamined Patent Application, First Publication No. 2005-327777
Patent Document 2: Japanese Unexamined Patent Application, First Publication No. 2008-169386
Patent Document 3: Japanese Unexamined Patent Application, First Publication No. Sho 59-137493
Patent Document 4: Japanese Unexamined Patent Application, First Publication No. Hei 07-126272

DISCLOSURE OF INVENTION

Technical Problems

An objective of the present invention is to provide a novel organosilicon compound and a method for producing thereof.

Another objective of the present invention is to provide a novel method for efficiently producing a high-purity succinic anhydride-functional organosilicon compound with good yield and at a reasonable manufacturing cost.

Further another objective of the present invention is to provide a curable silicone composition which possesses superior adhesive properties with respect to a poor-adhesive resin such as PPS and exhibits superior adhesive strength, even if the composition is cured at a relatively low temperature for a short period.

Technical Solution

The organosilicon compound of the present invention is characterized by having a succinic anhydride-functional group and an organosilicon group, and being represented by the following general formula (I):

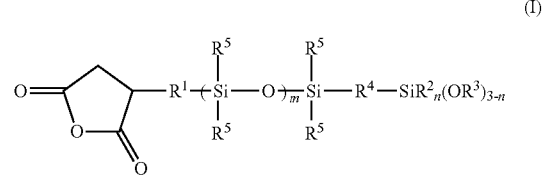

wherein
$R^1$ represents a substituted or non-substituted, saturated divalent hydrocarbon group having 3 to 12 carbon atoms, or a substituted or non-substituted divalent hydrocarbon group having 3 to 12 carbon atoms and having an unsaturated carbon-carbon double bond or triple bond, with the provisos that when $R^1$ is branched, no aliphatic unsaturated carbon-carbon bond is contained at the terminal of the molecular chain of the branched chain, and that when $R^1$ has a substituent, no aliphatic unsaturated carbon-carbon bond is contained at the terminal of the molecular chain of the substituent;
$R^2$ is a monovalent hydrocarbon group having 1 to 10 carbon atoms and having no aliphatic unsaturated bond at the terminal of the molecular chain;

$R^3$ is a monovalent hydrocarbon group having 1 to 18 carbon atoms and having no aliphatic unsaturated bond at the terminal of the molecular chain, or an alkoxyalkyl group having 2 to 18 carbon atoms;

$R^4$ is a substituted or non-substituted divalent hydrocarbon group having 1 to 12 carbon atoms, with the provisos that when $R^4$ is branched, no aliphatic unsaturated carbon-carbon bond is contained at the terminal of the molecular chain of the branched chain, and that when $R^4$ has a substituent, no aliphatic unsaturated carbon-carbon bond is contained at the terminal of the molecular chain of the substituent;

each $R^5$ is independently a monovalent hydrocarbon group having 1 to 10 carbon atoms and having no aliphatic unsaturated bond at the terminal of the molecular chain;

m is an integer ranging from 0 to 20; and n is 0, 1 or 2.

The method of the present invention for producing the organosilicon compound is characterized by reacting between an alkenyl-functional succinic anhydride represented by the following general formula (II):

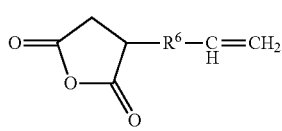

(II)

wherein $R^6$ is a substituted or non-substituted divalent hydrocarbon group having 1 to 10 carbon atoms; and an organosilicon compound represented by the following general formula (III):

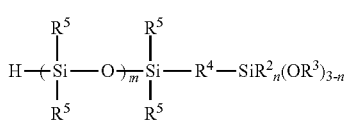

(III)

wherein $R^2$, $R^3$, $R^4$, $R^5$, m and n are the same as defined above in the aforementioned formula (I), in the presence of a hydrosilylation-reaction catalyst.

The organosilicon compound of the present invention is characterized by being used as an adhesion promoter for a curable silicone composition.

An alternative method of the present invention for producing a succinic anhydride-functional organosilicon compound is characterized by reacting an alkenyl-functional organosilicon compound and a maleic anhydride, wherein the alkenyl-functional organosilicon compound has a silicon-bonded hydrocarbon group that contains a structure: $H_2C=CH-CH_2-$ at the terminal of the molecular chain (namely, a hydrocarbon group which has a $H_2C=CH-CH_2-$ moiety at the terminal is bonded to a silicon atom), or a silicon-bonded 2-propenyl group (namely, a 2-propenyl group bonding to a silicon atom) as an alkenyl-functional group.

The curable silicone composition of the present invention comprises (A) an organopolysiloxane having at least two alkenyl groups in a molecule, in an amount of 100 parts by mass;

(B) an organopolysiloxane having at least two silicon-bonded hydrogen atoms in a molecule, in an amount in which an amount of the silicon-bonded hydrogen atom in the aforementioned component (B) ranges from 0.1 to 10 mol with respect to 1 mol of the alkenyl group of the aforementioned component (A);

(C) a hydrosilylation-reaction catalyst, in a catalytic amount; and (D) an acid anhydride having an alkoxy group bonding to a silicon atom or an alkoxyalkoxy group bonding to a silicon atom, in an amount ranging from 0.1 to 20 parts by mass.

Advantageous Effects of the Invention

The organosilicon compound of the present invention has characteristics of providing a curable silicone composition with superior adhesive properties with respect to a poor-adhesive resin such as PPS, and with superior adhesive strength, even if the compositions are cured at a relatively low temperature for a short period.

The latter of the aforementioned methods of the present invention for producing the succinic anhydride-functional organosilicon compound has characteristics of producing the target succinic anhydride-functional organosilicon compound by means of reacting a maleic anhydride and an alkenyl-functional organosilicon compound without using expensive raw materials such as a transition metal catalyst and the like. And since a maleic anhydride is an industrially cheap raw material, the method can drastically reduce the manufacturing cost of the succinic anhydride-functional organosilicon compound. Furthermore, since an alkenyl-functional organosilicon compound is used as a silicon source, it is unnecessary to use an Si—H containing organosilicon compound as in the latter of the aforementioned methods. As a result of using the alkenyl-functional organosilicon compound, the method of the present invention can produce the target product safely by using a general manufacturing facility.

The curable silicone composition of the present invention has characteristics in that superior adhesive properties with respect to a poor-adhesive resin such as PPS are exhibited, and superior adhesive strength is exhibited, even if the compositions are cured at a relatively low temperature for a short period.

BEST MODES FOR CARRYING OUT THE INVENTION

The organosilicon compounds of the present invention are described in detailed.

The organosilicon compound of the present invention is a succinic anhydride-functional organosilicon compound represented by the following general formula (I):

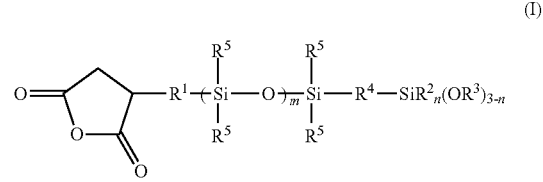

(I)

In the aforementioned formula (I), $R^1$ represents a substituted or non-substituted, saturated divalent hydrocarbon group having 3 to 12 carbon atoms, or a substituted or non-substituted divalent hydrocarbon group having 3 to 12 carbon atoms and having an unsaturated carbon-carbon double bond or triple bond. $R^1$ is preferably linear, but may be branched. When $R^1$ is branched, no aliphatic unsaturated carbon-carbon bond is contained at the terminal of the molecular chain of the branched chain. In addition, when $R^1$ has a substituent, no aliphatic unsaturated carbon-carbon bond is contained at the terminal of the molecular chain of the substituent.

As examples of $R^1$, mention may be made of an alkylene group having 3 to 12 carbon atoms, a substituted alkylene group which has a phenyl group and/or a cycloalkyl group as a pendant group, an alkylene/arylene/alkylene group, an arylene/alkylene group such as a —$C_6H_4$—$CH_2CH_2$— group, and a phenylene group.

Among these, $R^1$ is preferably an alkylene group having 3 to 12 carbon atoms, and in particular, preferably a linear alkylene group having 3 to 10 carbon atoms.

As examples of $R^1$, mention may be made of

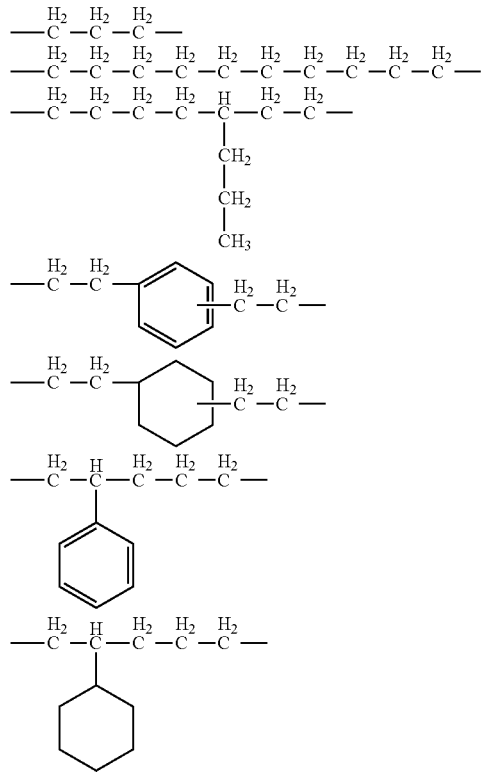

In the aforementioned formula (I), $R^2$ is a monovalent hydrocarbon group having 1 to 10 carbon atoms and having no aliphatic unsaturated bond at the terminal of the molecular chain. As examples thereof, mention may be made of, for example, alkyl groups such as a methyl group, an ethyl group, a propyl group, a butyl group, an isobutyl group, a tertiary butyl group, a pentyl group, a cyclopentyl group, a hexyl group, a cyclohexyl group, a decyl group and the like; halogenated alkyl groups such as a 3-chloropropyl group, a 3,3,3-trifluoropropyl group and the like; as well as, aryl groups such as a phenyl group, a tolyl group, a xylyl group and the like. $R^2$ is preferably an alkyl group, and in particular, preferably a methyl group.

In the aforementioned formula (I), $R^3$ is a monovalent hydrocarbon group having 1 to 18 carbon atoms and having no aliphatic unsaturated bond at the terminal of the molecular chain, or an alkoxyalkyl group having 2 to 18 carbon atoms. As examples of hydrocarbon groups, mention may be made of, for example, alkyl groups such as a methyl group, an ethyl group, a propyl group, a butyl group, a decyl group, a dodecyl group, a hexadecyl group and the like. As examples of alkoxyalkyl groups, mention may be made of, for example, alkoxyalkyl groups having 2 to 10 carbon atoms such as a methoxymethyl group, a methoxyethyl group, a methoxypropyl group, an ethoxymethyl group, an ethoxyethyl group, an ethoxypropyl group, a propoxymethyl group, a propoxyethyl group, a propoxypropyl group and the like. $R^3$ is preferably an alkyl group, and in particular, preferably an ethyl group or a methyl group.

In the aforementioned formula (I), $R^4$ is a substituted or non-substituted, saturated divalent hydrocarbon group having 1 to 12 carbon atoms, or a substituted or non-substituted divalent hydrocarbon group having 2 to 12 carbon atoms and having an unsaturated carbon-carbon double bond or triple bond. The aforementioned divalent hydrocarbon group is preferably linear, but may be branched, with the proviso that the aforementioned divalent hydrocarbon group has no aliphatic unsaturated bond at the terminal of the molecular chain of the branched chain or at the terminal of the molecular chain of the substituent.

As examples of $R^4$, mention may be made of an alkylene group having 1 to 12 carbon atoms such as chain —$CH_2$—, —$CH_2CH_2CH_2CH_2CH_2CH_2CH_2CH_2CH_2CH_2CH_2CH_2$—, —$CH(CH_3)$—$CH_2$— and the like; a substituted alkylene group having 8 to 21 carbon atoms having a phenyl group or a cycloalkyl group as a pendant group; an alkylene/arylene/alkylene group having 8 to 21 carbon atoms such as —$CH_2CH_2$—$C_6H_4$—$CH_2CH_2$— and the like; an arylene/alkylene group having 8 to 21 carbon atoms such as —$C_6H_4$—$CH_2CH_2$— and the like; and a phenylene group. Among these, $R^4$ is preferably an alkylene group having 1 to 12 carbon atoms, and more preferably a linear alkylene group having 2 to 9 carbon atoms.

As examples of $R^4$, mention may be made of

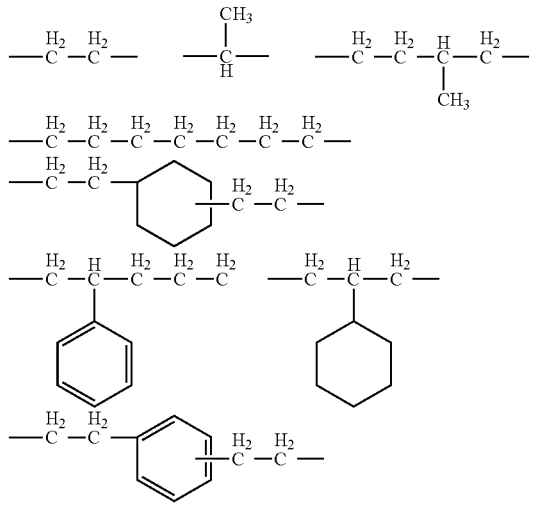

In the aforementioned formula (I), each $R^5$ is independently a monovalent hydrocarbon group having 1 to 10 carbon atoms and having no aliphatic unsaturated bond at the terminal of the molecular chain. As examples thereof, mention may be made of, for example, alkyl groups such as a methyl group, an ethyl group, a propyl group, a butyl group, an isobutyl group, a tertiary butyl group, a pentyl group, a cyclopentyl group, a hexyl group, a cyclohexyl group, a decyl group and the like; halogenated alkyl groups such as a 3-chloropropyl group, a 3,3,3-trifluoropropyl group and the like; as well as, aryl groups such as a phenyl group, a tolyl group, a xylyl group and the like. Each $R^5$ is independently preferably selected from the group consisting of an alkyl group and a phenyl group, and in particular, preferably selected from the group consisting of a methyl group, an ethyl group, a cyclohexyl group and a phenyl group. A methyl group is most preferred. As examples of —Si($R^5$)($R^5$)—, mention may be made of the following structures:

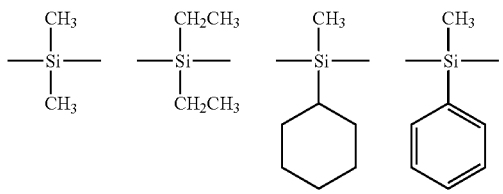

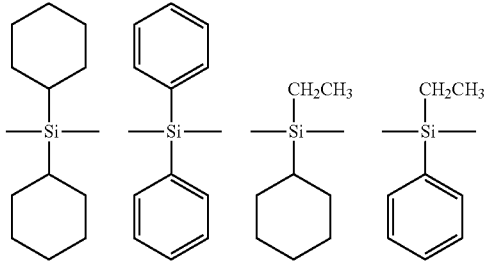

In the aforementioned formula (I), n is 0, 1 or 2, and in particular, preferably 0 or 1.

In the aforementioned formula (I), m is an integer ranging from 0 to 20, preferably an integer ranging from 0 to 10, more preferably an integer ranging from 0 to 2, and in particular, preferably 1 or 2.

As examples of novel succinic anhydride-functional organosilicon compounds represented by the aforementioned formula (I), the following compounds can be mentioned.

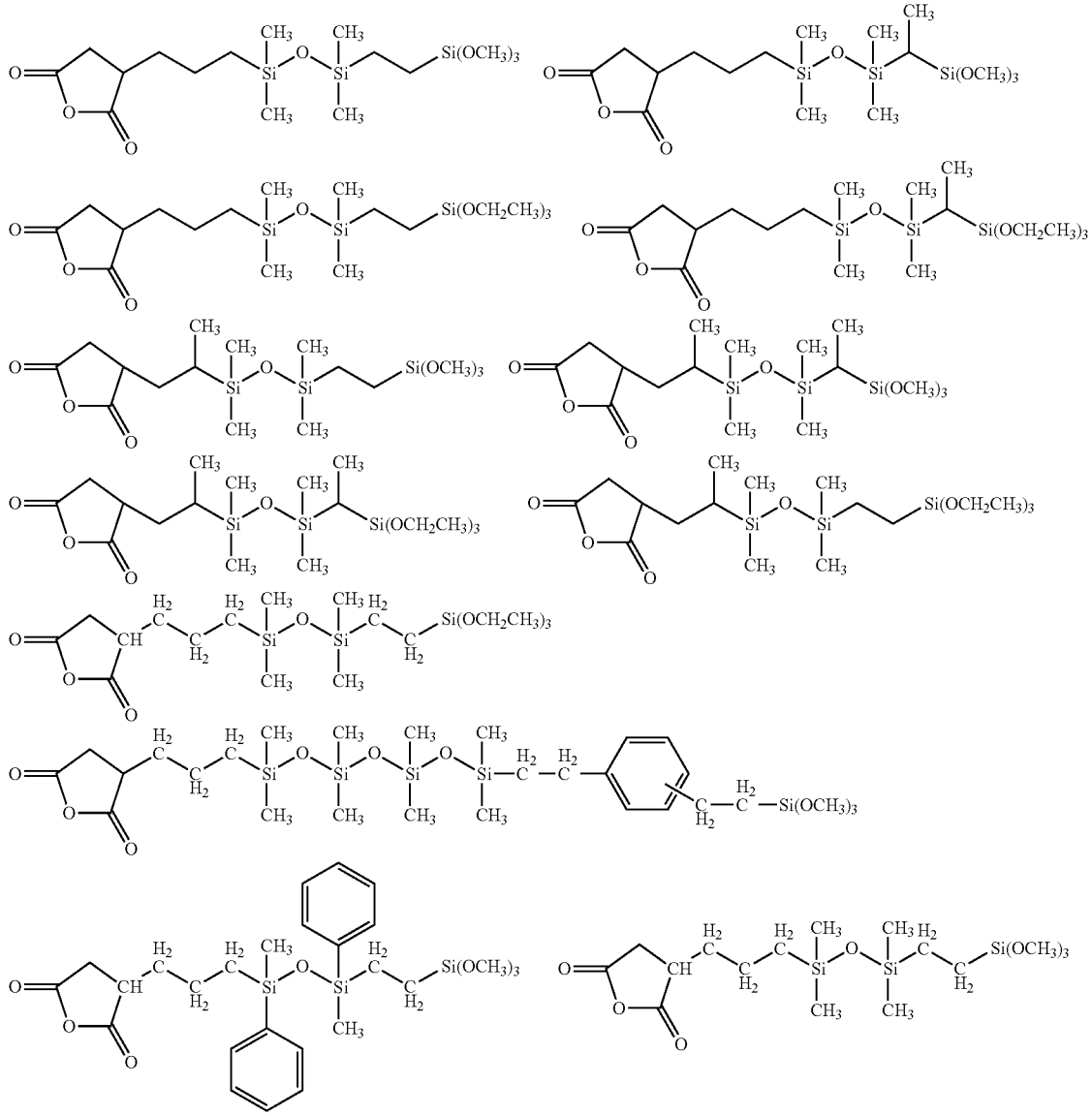

-continued

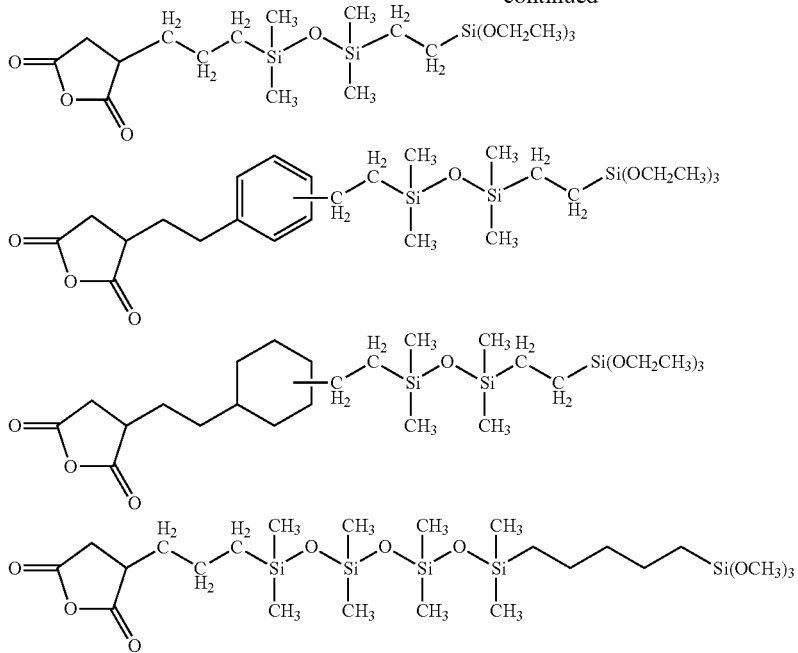

Among these, the following compounds are particularly preferred, since a high-purity product can be easily produced by distillation, and raw materials are easily commercially available.

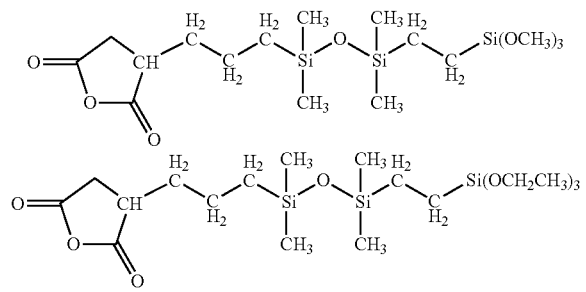

The novel compound represented by the aforementioned general formula (I) can be produced by reacting an alkenyl-functional succinic anhydride represented by the following general formula (II):

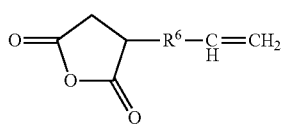

and an organosilicon compound represented by the following general formula (III):

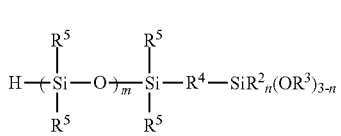

In the aforementioned formula (II), $R^6$ is a substituted or non-substituted divalent hydrocarbon group having 1 to 10 carbon atoms, and may be a substituted or non-substituted divalent hydrocarbon group having 2 to 10 carbon atoms and having an unsaturated carbon-carbon double bond. The aforementioned divalent hydrocarbon group is preferably linear, but may be branched, with the provisos that when the aforementioned divalent hydrocarbon group is a branched chain, no aliphatic unsaturated bond is present at the terminal of the molecular chain of the branched chain, and that when the aforementioned divalent hydrocarbon group has a substituent, no aliphatic unsaturated bond is present at the terminal of the molecular chain of the substituent. $R^6$ is in particular, preferably a linear alkylene group having 2 to 8 carbon atoms. In the aforementioned formula (III), $R^2$, $R^3$, $R^4$, $R^5$, m and n are the same as defined above in the aforementioned formula (I).

The organosilicon compound represented by the aforementioned formula (III) can be easily produced by means of a hydrosilylation reaction between a diorganosiloxane oligomer of which both terminals of the molecular chain are capped with diorganohydrogensilyl groups and an alkenyl group-containing alkoxysilane and/or alkenyl group-containing alkoxyalkoxysilane. The molar ratio of the diorganosiloxane oligomer of which both terminals of the molecular chain are capped with diorganohydrogensilyl groups to the alkenyl group-containing alkoxysilane and/or alkenyl group-containing alkoxyalkoxysilane preferably ranges from 0.8:1.0 to 1.2:1.0.

In the case of reacting the alkenyl-functional succinic anhydride (II) and the organosilicon compound (III), the organosilicon compound (III) is preferably used in an amount ranging from 1.0 to 10.0 mol and more preferably used in an amount ranging from 1.0 to 1.5 mol, with respect to one mol of the alkenyl-functional succinic anhydride (II). By using one or more mol of the organosilicon compound (III) with respect to one mol of the alkenyl-functional succinic anhydride (II), prevention of a large amount of unreacted alkenyl-functional succinic anhydride (II) remaining is possible, and a yield of a target product can be increased. On the other hand, by using 10.0 mol or less of the organosilicon compound (III) with respect to one mol of the alkenyl-functional succinic anhydride (II), reduction of a pot yield in the production which is caused by a large amount of the organosilicon compound (III) remaining can be controlled, and this is economically advantageous.

As a method for introducing the alkenyl-functional succinic anhydride (II) and the organosilicon compound (III) in a reactor, any method can be used. The mixing molar ratio of the aforementioned compounds is preferably present within the aforementioned range. In addition, the organosilicon compound (III) may be introduced in the alkenyl-functional succinic anhydride (II) under heating conditions, or vice versa may be applied. The temperature in the case of carrying out the reaction under heating is preferably within a preferable range of the reaction temperature described below.

The temperature of the reaction between the alkenyl-functional succinic anhydride (II) and the organosilicon compound (III) is not particularly restricted, as long as the intended reaction can proceed. The aforementioned reaction can be carried out in any temperature and may be carried out under heating. In this case, the reaction temperature preferably ranges from 100° C. to 180° C. By specifying the reaction temperature to 100° C. or higher, the reaction rate is increased and the reaction period for producing the desirable product can be shortened. Therefore, this is economically advantageous. On the other hand, by specifying the reaction temperature to 180° C. or lower, the possibility of coloration of the product can be reduced.

The aforementioned reaction can be carried out under any pressure, and in particular, there is no restriction of pressure. In the case of failing to reach the desirable temperature at the time of heating under normal pressure or in the case of taking a remarkably long time to complete the reaction under normal pressure, depending on the boiling points of raw materials used, the reaction may be carried out under exerting pressure. In this case, any pressure can be used, but preferably ranges from 1 kPa to 5 kPa. By carrying out the aforementioned reaction under 1 kpa or more, only a slight reduction in the yield of the target product may occur.

The aforementioned reaction is preferably carried out under an atmosphere of inert gas such as nitrogen or argon. In addition, the moisture content of the alkenyl-functional succinic anhydride (II) and the organosilicon compound (III) is preferably reduced as small as possible.

In addition, in the aforementioned reaction, an organic solvent containing no active hydrogen, selected from, for example, toluene, xylene, benzene, hexane, ethylene chloride, chloroform, trichloroethylene, and cyclohexane may be used, if necessary. When the aforementioned reaction is carried out with a low polar solvent, the reaction efficacy may be reduced in some cases. For this reason, use of none of the aforementioned organic solvents is generally preferable.

A catalyst for use in the hydrosilylation reaction between the compound of the aforementioned formula (II) and the compound of the aforementioned formula (III) is a catalyst for accelerating the reaction of adding the silicon-bonded hydrogen atom in the aforementioned formula (III) (namely, a hydrogen atom bonding to a silicon atom) to the alkenyl group in the aforementioned formula (II). As examples thereof, mention may be made of, for example, a catalyst based on a VIII transition metal in the long format of the Periodic Table. A platinum-based catalyst is preferred. As examples of the aforementioned platinum-based catalyst, mention may be made of chloroplatinic acid, an alcohol solution of chloroplatinic acid, a platinum-olefin complex, a platinum-alkenylsiloxane complex, and a platinum-carbonyl complex. The catalytic amount used is not particularly restricted as long as the intended reaction can proceed.

The novel organosilicon compound of the present invention represented by the aforementioned formula (I) is useful for an adhesion promoter for a curable silicone composition. The curable silicone composition is a well-known curable silicone composition in the art, and is exemplified by an addition reaction-curable silicone composition which can be crosslinked and cured by means of an addition reaction between a silicone compound having an unsaturated group at the terminal of the molecular chain and an Si—H containing silicone compound, as well as a condensation reaction-curable silicone composition which can be crosslinked and cured by means of a condensation reaction of a silicone compound having a hydroxy group or a hydrolysable group such as an alkoxy group and the like. In particular, the novel organosilicon compound represented by the aforementioned formula (I) is useful for an adhesion promoter for an addition reaction-curable silicone composition. For example, an addition reaction-curable silicone composition containing the novel organosilicon compound of the present invention exhibits superior adhesive properties at low temperature and adhesive strength with respect to a poor-adhesive resin such as PPS (polyphenylene sulfide), die-casted aluminum and the like.

Another method of the present invention for producing a succinic anhydride-functional compound is described in detail below. This method of the present invention is characterized by reacting an alkenyl-functional organosilicon compound represented by the following general formula (V):

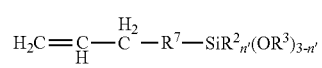

(V)

and
a maleic anhydride represented by the following formula (VI):

(VI)

In the aforementioned formula (V), $R^2$ is a monovalent hydrocarbon group having 1 to 10 carbon atoms and having no aliphatic unsaturated bond at the terminal of the molecular chain. As examples thereof, mention may be made of, for example, alkyl groups such as a methyl group, an ethyl group, a propyl group, a butyl group, an isobutyl group, a tertiary butyl group, a pentyl group, a cyclopentyl group, a hexyl group, a cyclohexyl group, a decyl group and the like; halogenated alkyl groups such as a 3-chloropropyl group, a 3,3,3-trifluoropropyl group and the like; as well as, aryl groups such as a phenyl group, a tolyl group, a xylyl group and the like. $R^2$ is preferably an alkyl group, and in particular, preferably a methyl group.

In the aforementioned formula (V), $R^3$ is a monovalent hydrocarbon group having 1 to 18 carbon atoms and having no aliphatic unsaturated bond at the terminal of the molecular chain, or an alkoxyalkyl group having 2 to 18 carbon atoms. As examples of hydrocarbon groups, mention may be made of, for example, alkyl groups such as a methyl group, an ethyl group, a propyl group, a butyl group, a decyl group, a dodecyl group, a hexadecyl group and the like. As examples of alkoxyalkyl groups, mention may be made of, for example, alkoxyalkyl groups having 2 to 10 carbon atoms such as a methoxymethyl group, a methoxyethyl group, a methoxypropyl group, an ethoxymethyl group, an ethoxyethyl group, an ethoxypropyl group, a propoxymethyl group, a propoxyethyl group, a propoxypropyl group and the like. $R^3$ is preferably an alkyl group, and in particular, preferably an ethyl group or a methyl group.

In the aforementioned formula (V), $R^7$ represents a single bond directly bonding between —$CH_2$— at the left of $R^7$ and Si atom at the right of $R^7$ in the aforementioned formula (V), a saturated divalent hydrocarbon group having 1 to 21 carbon atoms, or a substituted or non-substituted divalent hydrocarbon group having 2 to 21 carbon atoms and having an unsaturated carbon-carbon double bond or triple bond. The aforementioned divalent hydrocarbon group is preferably linear, but may be branched, with the provisos that when the aforementioned divalent hydrocarbon group is a branched chain, no aliphatic unsaturated carbon-carbon bond is contained at the terminal of the molecular chain of the branched chain, and that when the aforementioned divalent hydrocarbon group has a substituent, no aliphatic unsaturated carbon-carbon bond is contained at the terminal of the molecular chain of the substituent.

As examples of $R^7$, mention may be made of an alkylene group having 1 to 15 carbon atoms such as chain —$CH_2$—, —$CH_2CH_2CH_2CH_2CH_2CH_2CH_2CH_2CH_2CH_2CH_2CH_2$—, —$CH(CH_3)$—$CH_2$— and the like; a substituted alkylene group having 8 to 21 carbon atoms having a phenyl group or a cycloalkyl group as a pendant group; an alkylene/arylene/alkylene group having 8 to 21 carbon atoms such as —$CH_2CH_2$—$C_6H_4$—$CH_2CH_2$— and the like; an arylene/alkylene group having 8 to 21 carbon atoms such as —$C_6H_4$—$CH_2CH_2$— and the like; and a phenylene group. Among these, $R^7$ is preferably an alkylene group having 1 to 15 carbon atoms, and more preferably a linear alkylene group having 2 to 9 carbon atoms.

Also, $R^7$ may be a group represented by the following general formula:

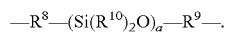

—$R^8$—$(Si(R^{10})_2O)_a$—$R^9$—.

In the aforementioned formula, each $R^8$ and $R^9$ is independently a substituted or non-substituted saturated divalent hydrocarbon group having 1 to 15 carbon atoms, or a substituted or non-substituted divalent hydrocarbon group having 2 to 15 carbon atoms and having an unsaturated carbon-carbon double bond or triple bond. The aforementioned divalent hydrocarbon group is preferably linear, but may be branched, with the provisos that when the divalent hydrocarbon group is a branched chain, no aliphatic unsaturated carbon-carbon bond is contained at the terminal of the molecular chain of the branched chain, and that when the divalent hydrocarbon group has a substituent, no aliphatic unsaturated carbon-carbon bond is contained at the terminal of the molecular chain of the substituent. $R^8$ and $R^9$ are preferably alkylene groups having 1 to 15 carbon atoms, and more preferably alkylene groups having 2 to 6 carbon atoms. In the aforementioned formula, a is an integer ranging from 1 to 10, preferably an integer ranging from 2 to 4. $R^{10}$ is a monovalent hydrocarbon group having 1 to 10 carbon atoms and having no aliphatic unsaturated bond at the terminal of the molecular chain. As examples thereof, mention may be made of, for example, alkyl groups such as a methyl group, an ethyl group, a propyl group, a butyl group, an isobutyl group, a tertiary butyl group, a pentyl group, a cyclopentyl group, a hexyl group, a cyclohexyl group, a decyl group and the like; halogenated alkyl groups such as a 3-chloropropyl group, a 3,3,3-trifluoropropyl group and the like; as well as, aryl groups such as a phenyl group, a tolyl group, a xylyl group and the like. $R^{10}$ is preferably an alkyl group, and in particular, preferably a methyl group.

In the aforementioned formula (V), n' is 0, 1, 2 or 3, and in particular, preferably 0, 1 or 2, and more preferably 0 or 1.

As examples of alkenyl-functional organosilicon compounds represented by the aforementioned formula (V), the following compounds can be mentioned.

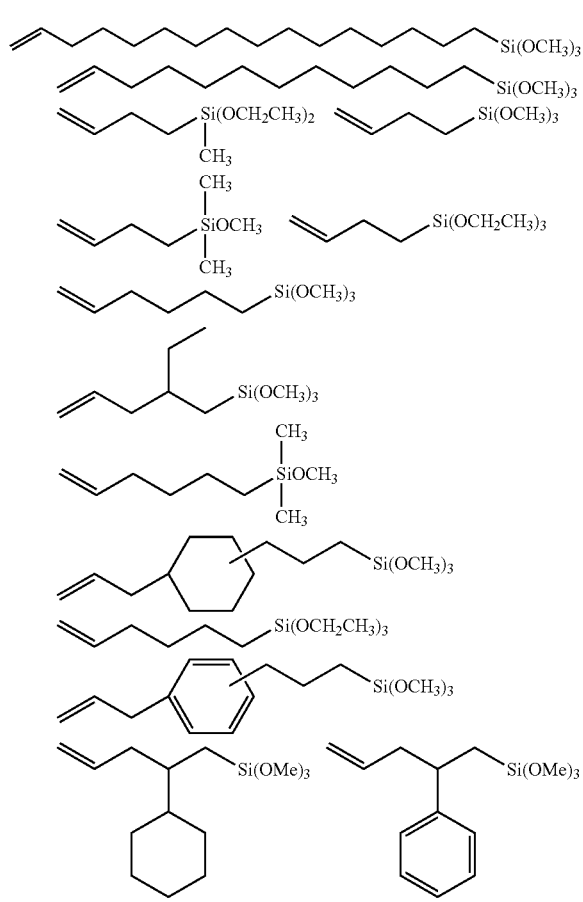

Among these, the following compounds are particularly preferred.

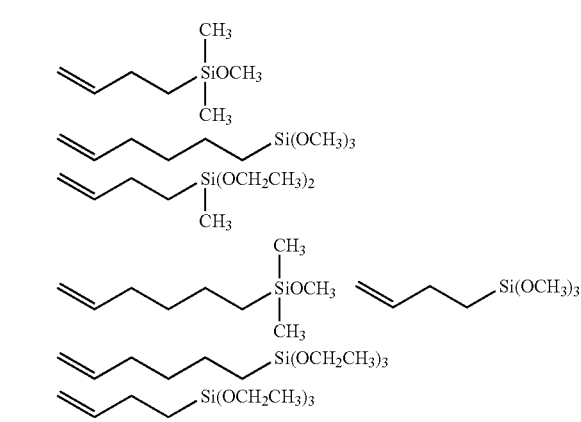

The succinic anhydride-functional organosilicon compound produced by the aforementioned method of the present invention is represented by the following general formula (IV):

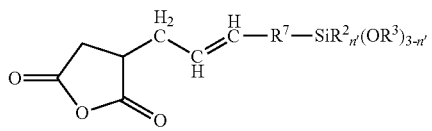

wherein $R^2$, $R^3$, $R^7$ and n' are the same as defined above in the aforementioned formula (V).

The method of the present invention is possible to produce the succinic anhydride-functional organosilicon compound represented by the aforementioned formula (IV) by means of reacting the alkenyl-functional organosilicon compound represented by the aforementioned formula (V) and the maleic anhydride represented by the aforementioned formula (VI).

As examples of the succinic anhydride-functional organosilicon compound, the following compounds can be mentioned.

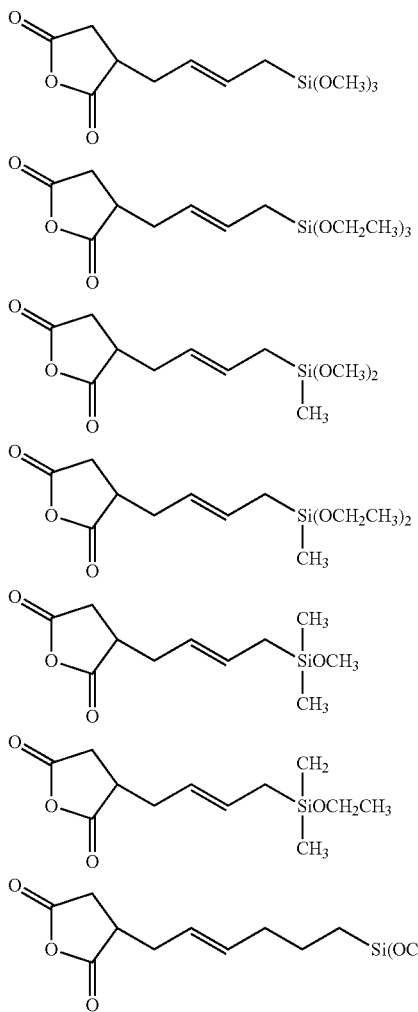

-continued

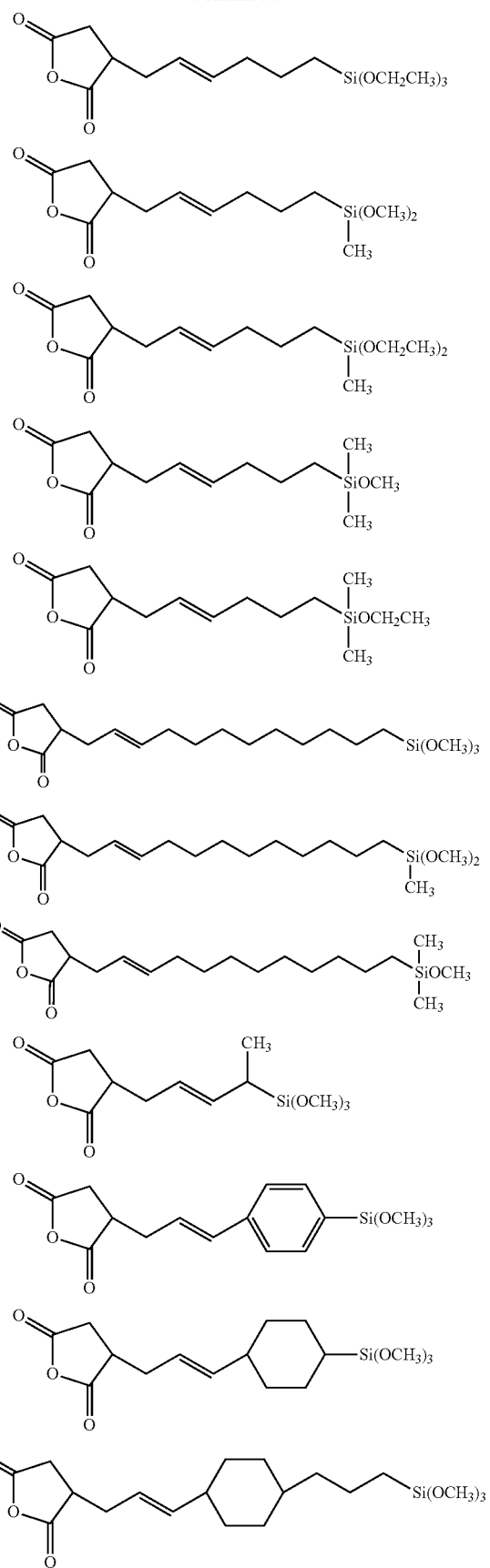

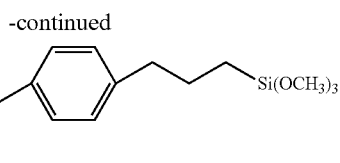

Among these, the following compounds are particularly preferred, since a high-purity target product can be easily produced by distillation.

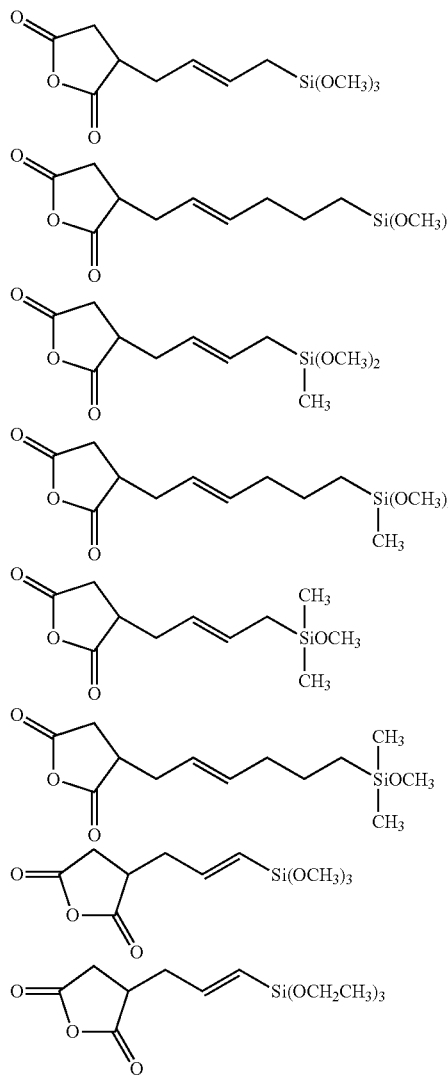

The method of the present invention for producing a succinic anhydride-functional organosilicon compound is characterized by reacting the alkenyl-functional organosilicon compound of formula (V) and maleic anhydride, in particular, reacting them under heating. The mixing molar ratio of the alkenyl-functional organosilicon compound and maleic anhydride is not particularly restricted, but the alkenyl-functional organosilicon compound is preferably used in an amount ranging from 1.0 to 10.0 mol and more preferably used in an amount ranging from 1.0 to 5.0 mol, with respect to one mol of the maleic anhydride. By using one or more mol of the alkenyl-functional organosilicon compound with respect to one mol of the maleic anhydride, a large amount of unreacted maleic anhydride can be prevented from remaining, and when unreacted maleic anhydride remains, a problem that solid maleic anhydride is difficult to separate from the target product can be avoided. On the other hand, by using 10.0 mol or less of the alkenyl-functional organosilicon compound with respect to one mol of the maleic anhydride, a reduction of a pot yield in the production which is caused by a large amount of the alkenyl-functional organosilicon compound remaining can be controlled, and this is economically advantageous.

As a method for introducing the alkenyl-functional organosilicon compound and maleic anhydride in a reactor, any method can be used. The mixing molar ratio of the alkenyl-functional organosilicon compound and maleic anhydride is preferably present within the aforementioned range. In addition, the maleic anhydride may be introduced in the alkenyl-functional organosilicon compound under heating conditions, or vice versa may be applied. The temperature in the case of carrying out the reaction under heating is preferably within a preferable range of the reaction temperature described below.

The temperature of the reaction between the alkenyl-functional organosilicon compound and maleic anhydride is not particularly restricted, as long as the intended reaction can proceed. The aforementioned reaction can be carried out at any temperature and may be carried out under heating. The reaction temperature differs dependent on the pressure in the reactor and the type of alkenyl-functional organosilicon compound used, but in this case, the reaction temperature preferably ranges from 100° C. to 180° C. By employing a reaction temperature of 100° C. or higher, the reaction rate increases and the reaction period for producing a desirable product can be shortened. Therefore, this is economically advantageous. On the other hand, by employing a reaction temperature of 180° C. or lower, it is possible to control a side reaction caused by the polymerization of the alkenyl-functional organosilicon compound, and it is possible to increase the yield of the target product. For example, when 5-hexenyltrimethoxysilane is used as the alkenyl-functional organosilicon compound, the reaction temperature preferably ranges from 140° C. to 160° C. In the case that the reaction temperature of a reaction mixture cannot reach the intended temperature because of a lower reflux temperature, the reaction may be carried out by using the solvent described below or under pressure.

In addition, in the aforementioned reaction between the alkenyl-functional organosilicon compound and maleic anhydride, an organic solvent containing no active hydrogen, selected from, for example, toluene, xylene, benzene, hexane, ethylene chloride, chloroform, trichloroethylene, and cyclohexane may be used, if necessary. However, if a reduction of a pot yield and decrease of the target product by using the solvent is occurred, the aforementioned reaction may be carried out without using the solvent. When the aforementioned reaction is carried out with a low polar solvent, the reaction efficacy may be reduced in some cases. For this reason, use of none of the aforementioned organic solvents is generally preferable.

The aforementioned reaction can be carried out under any pressure, and in particular, there is no restriction of the pressure. In the case of failing to reach the desirable temperature at the time of heating under normal pressure or in the case of taking a remarkably long time to complete the reaction under normal pressure, depending on the boiling points of the raw materials used, the reaction may be carried out under pressure. In this case, any pressure can be used, but preferably ranges from 1 kPa to 5 kPa. By carrying out the aforementioned reaction under 1 kPa or more, only a slight reduction in the yield of the target product may occur.

The aforementioned reaction between the alkenyl-functional organosilicon compound and maleic anhydride is preferably carried out under an atmosphere of inert gas such as nitrogen or argon. In addition, the moisture content of the alkenyl-functional organosilicon compound and maleic anhydride is preferably reduced as small as possible.

Though the method of the present invention is characterized by reacting the alkenyl-functional organosilicon compound and maleic anhydride, it is desirable that the inhibitor is added to the reaction system in order to prevent the polymerization reaction of the alkenyl-functional organosilicon compound which is occurred under this reaction condition as side reaction. As examples of the aforementioned inhibitor, mention may be made of an inhibitor selected from the group consisting of a phenothiazine, hindered phenol-type compound, amine-type compound, quinone-type compound and β-diketone compound. Type and amount of the inhibitor is not restricted, as long as the reaction between the alkenyl-functional organosilicon compound and maleic anhydride can proceed, and the polymerization reaction of the alkenyl-functional organosilicon compound can be prevented by using the inhibitor. However, there is no necessity of using the inhibitor, when the polymerization reaction of the alkenyl-functional organosilicon compound does not become a problem.

The curable silicone compositions of the present invention are described in detail below. Component (A) is a main component of the composition of the present invention, and is an organopolysiloxane having at least two alkenyl groups in a molecule. As examples of the alkenyl group in the aforementioned component (A), mention may be made of a vinyl group, an allyl group, a butenyl group, a pentenyl group, a hexenyl group and a heptenyl group. A vinyl group is preferred. In addition, as examples of silicon-bonded organic groups other than the alkenyl group in the aforementioned component (A), that is, organic groups bonding to the silicon atoms, mention may be made of, alkyl groups such as a methyl group, an ethyl group, a propyl group, a butyl group, a pentyl group, a hexyl group and the like; aryl groups such as a phenyl group, a tolyl group, a xylyl group and the like; aralkyl groups such as a benzyl group, a phenethyl group and the like; and halogenated alkyl groups such as a chloromethyl group, a 3-chloropropyl group, a 3,3,3-trifluoropropyl group and the like. The silicon-bonded organic groups other than the alkenyl group in the aforementioned component (A) is preferably selected from a methyl group and a phenyl group. The molecular structure of component (A) is not particularly restricted, and examples thereof may include a linear structure, a branched structure, a cyclic structure, a network structure and a linear structure having a partially branched structure. The aforementioned component (A) is preferably a mixture of (A1) a linear organopolysiloxane having at least two alkenyl groups in a molecule and (A2) a branched organopolysiloxane having at least two alkenyl groups in a molecule.

As examples of organopolysiloxanes of the aforementioned component (A1), mention may be made of a copolymer of methylvinylsiloxane and dimethylsiloxane of which both terminals of the molecular chain are capped with trimethylsiloxy groups, a methylvinylpolysiloxane of which both terminals of the molecular chain are capped with trimethylsiloxy groups, a copolymer of methylphenylsiloxane, methylvinylsiloxane and dimethylsiloxane of which both terminals of the molecular chain are capped with trimethylsiloxy groups, a dimethylpolysiloxane of which both terminals of the molecular chain are capped with dimethylvinylsiloxy groups, a methylvinylpolysiloxane of which both terminals of the molecular chain are capped with dimethylvinylsiloxy groups, a copolymer of methylvinylsiloxane and dimethylsiloxane of which both terminals of the molecular chain are capped with dimethylvinylsiloxy groups, and a copolymer of methylphenylsiloxane, methylvinylsiloxane and dimethylsiloxane of which both terminals of the molecular chain are capped with dimethylvinylsiloxy groups.

The viscosity of the aforementioned component (A1) at 25° C. is not particularly restricted, and preferably ranges from 10 to 1,000,000 mPa·s, and in particular, preferably ranges from 100 to 100,000 mPa·s.

On the other hand, as the organopolysiloxane of the aforementioned component (A2), an organopolysiloxane formed from a siloxane unit represented by the formula: $R_3SiO_{1/2}$, a siloxane unit represented by the formula: $R_2R'SiO_{1/2}$ and a siloxane unit represented by the formula: $SiO_{4/2}$ is preferred. In the aforementioned formulae, R is a monovalent hydrocarbon group other than an alkenyl group. As examples thereof, mention may be made of, for example, alkyl groups such as a methyl group, an ethyl group, a propyl group, a butyl group, a pentyl group, a hexyl group, a heptyl group and the like; aryl groups such as a phenyl group, a tolyl group, a xylyl group, a naphthyl group and the like; aralkyl groups such as a benzyl group, a phenethyl group and the like; and halogenated alkyl groups such as a chloromethyl group, a 3-chloropropyl group, a 3,3,3-trifluoropropyl group and the like. In addition, in the aforementioned formula, R' is an alkenyl group. As examples thereof, mention may be made of, for example, a vinyl group, an allyl group, a butenyl group, a pentenyl group, a hexenyl group and a heptenyl group.

As examples of organopolysiloxanes of the aforementioned component (A2), mention may be made of an organopolysiloxane copolymer formed from a siloxane unit represented by the formula: $(CH_3)_3SiO_{1/2}$, a siloxane unit represented by the formula: $(CH_3)_2(CH_2{=}CH)SiO_{1/2}$ and a siloxane unit represented by the formula: $SiO_{4/2}$, and an organopolysiloxane copolymer formed from a siloxane unit represented by the formula: $(C_6H_5)(CH_3)_2SiO_{1/2}$, a siloxane unit represented by the formula: $(CH_3)_2(CH_2{=}CH)SiO_{1/2}$ and a siloxane unit represented by the formula: $SiO_{4/2}$.

The mass average molecular weight of the aforementioned component (A2) calculated on the basis of a polystyrene standard by means of gel permeation chromatography is not particularly restricted, and preferably ranges from 100 to 10,000 in any case.

The ratio of the aforementioned component (A1) and component (A2) is not particularly restricted. The mass ratio (A1:A2) preferably ranges form 95:5 to 50:50, more preferably ranges from 90:10 to 60:40, and in particular, preferably ranges from 90:10 to 70:30. By specifying the mass ratio of the aforementioned component (A2) to at least the lower limit of the aforementioned range, large reduction of physical strength of a cured product obtained can be prevented. On the other hand, by specifying the mass ratio of the aforementioned component (A2) to at most the upper limit of the aforementioned range, large reduction of elongation of a cured product obtained can be prevented.

The aforementioned component (B) is a crosslinking agent of the composition of the present invention, and is an organopolysiloxane having at least two silicon-bonded hydrogen atoms (namely, hydrogen atoms bonding to silicon atoms) in a molecule. The bonding position of the aforementioned silicon-bonded hydrogen atom in the aforementioned component (B) is not particularly restricted, and may be, for example, at the terminal of the molecular chain and/or at the side chain of the molecular chain. As examples of the silicon-bonded organic groups in the aforementioned component (B), mention may be made of, for example, alkyl groups such as a methyl group, an ethyl group, a propyl group, a butyl group, a pentyl group, a hexyl group, a heptyl group and the like; aryl groups such as a phenyl group, a tolyl group, a xylyl group, a naphthyl group and the like; aralkyl groups such as a benzyl group, a phenethyl group and the like; and halogenated alkyl groups such as a chloromethyl group, a 3-chloropropyl group, a 3,3,3-trifluoropropyl group and the like. A methyl group and/or a phenyl group are preferred. The molecular structure of the aforementioned component (B) is not particularly restricted, and examples thereof may include a linear structure, a branched structure, a cyclic structure, a network structure and a linear structure having a partially branched structure. A linear structure is preferred.

As examples of organopolysiloxanes of the aforementioned component (B), mention may be made of a methylhydrogenpolysiloxane of which both terminals of the molecular chain are capped with trimethylsiloxy groups, a copolymer of methylhydrogensiloxane and dimethylsiloxane of which both terminals are capped with trimethylsiloxy groups, a copolymer of methylphenylsiloxane, methylhydrogensiloxane and dimethylsiloxane of which both terminals of the molecular chain are capped with trimethylsiloxy groups, a dimethylpolysiloxane of which both terminals of the molecular chain are capped with dimethylhydrogensiloxy groups, a copolymer of methylphenylsiloxane and dimethylsiloxane of which both terminals of the molecular chain are capped with dimethylhydrogensiloxy groups, a methylphenylpolysiloxane of which both terminals of the molecular chain are capped with dimethylhydrogensiloxy groups, an organopolysiloxane copolymer formed from a siloxane unit represented by the formula: $R_3SiO_{1/2}$, a siloxane unit represented by the formula: $R_2HSiO_{1/2}$, and a siloxane unit represented by the formula: $SiO_{4/2}$, an organopolysiloxane copolymer formed from a siloxane unit represented by the formula: $R_2HSiO_{1/2}$, and a siloxane unit represented by the formula: $SiO_{4/2}$, an organopolysiloxane copolymer formed from a siloxane unit represented by the formula: $RHSiO_{2/2}$, a siloxane unit represented by the formula: $RSiO_{3/2}$ or a siloxane unit represented by the formula: $HSiO_{3/2}$, and a mixture of two or more types of the aforementioned organopolysiloxanes. In the aforementioned formulae, R is a monovalent hydrocarbon group other than an alkenyl group. As examples thereof, mention may be made of, for example, alkyl groups such as a methyl group, an ethyl group, a propyl group, a butyl group, a pentyl group, a hexyl group, a heptyl group and the like; aryl groups such as a phenyl group, a tolyl group, a xylyl group, a naphthyl group and the like; aralkyl groups such as a benzyl group, a phenethyl group and the like; and halogenated alkyl groups such as a chloromethyl group, a 3-chloropropyl group, a 3,3,3-trifluoropropyl group and the like.

The viscosity of the aforementioned component (B) at 25° C. is not particularly restricted, and preferably ranges from 1 to 500,000 mPa·s, and in particular, preferably ranges from 5 to 100,000 mPa·s. By using component (B) having the viscosity of 1 mPa·s or more, large reduction of mechanical strength of the obtained cured product can be prevented. On the other hand, by using component (B) having a viscosity of 500,000 mPa·s or less, large reduction of workability of the obtained composition can be prevented.

The amount of the aforementioned component (B) is specified so that the amount of silicon-bonded hydrogen atoms in component (B) ranges from 0.1 to 10 mol, and preferably ranges from 0.1 to 5 mol, with respect to one mol of the alkenyl group in component (A). When the amount of the silicon-bonded hydrogen atom in component (B) with respect to the alkenyl group of component (A) is not less than the lower limit of the aforementioned range, failing to sufficiently cure the obtained composition can be prevented. On the other hand, when the amount is not more than the upper limit of the aforementioned range, change in physical properties of the obtained cured product over time can be controlled in a small range.

The hydrosilylation-reaction catalyst of component (C) is a catalyst for accelerating curing of the composition of the present invention. As examples thereof, mention may be made of a platinum-based catalyst, a rhodium-based catalyst, and a palladium-based catalyst. In particular, a platinum-based catalyst is preferred. As examples of the aforementioned platinum-based catalyst, mention may be made of platinum-based compounds such as platinum fine powder, platinum black, platinum-supported silica fine powder, platinum-supported activated carbon, chloroplatinic acid, an alcohol solution of chloroplatinic acid, a platinum-olefin complex, a platinum-alkenylsiloxane complex and the like.

The amount of the aforementioned component (C) is a catalytic amount. More particularly, a metal atom in the catalyst is preferably contained in an amount ranging from 0.01 to 1,000 ppm on the basis of mass with respect to the amount of the composition of the present invention. When the amount of the aforementioned component (C) is 0.01 ppm or more, failing to sufficiently proceed curing of the obtained composition can be prevented. On the other hand, when the amount is 1,000 ppm or less, a sufficient curing rate can be obtained and at the same time, remarkable coloration of the cured product can be prevented.

The aforementioned component (D) is a component for improving adhesive properties of the composition of the present invention, and is an acid anhydride having an alkoxy group bonding to a silicon atom or an alkoxyalkoxy group bonding to a silicon atom. The aforementioned component (D) is a symmetric anhydride of a monocarboxylic acid such as acetic anhydride, benzoic anhydride and the like; or a cyclic anhydride of a polycarboxylic acid such as succinic anhydride, phthalic anhydride, trimellitic anhydride, pyromellitic anhydride, endomethylene tetrahydrophthalic anhydride, methyl endomethylene tetrahydrophthalic anhydride, methyltetrahydrophthalic anhydride, diphenic anhydride and the like, in which a group containing an alkoxy group bonding to a silicon atom or an alkoxyalkoxy group bonding to a silicon atom is bonded as a substituent. The aforementioned cyclic anhydride is preferred.

The aforementioned component (D) is preferably at least one acid anhydride-functional organosilicon compound selected from the group consisting of compounds represented by the following formulae (1) to (4). In particular, component (D) is preferably at least one succinic anhydride-functional organosilicon compound selected from the group consisting of compounds represented by the following formulae (1) and (2).

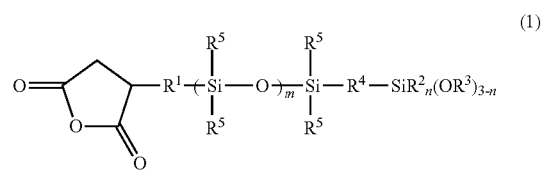

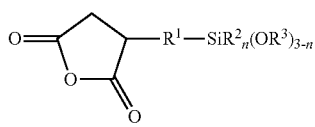
(2)

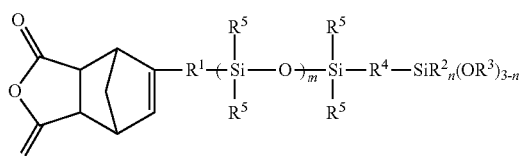
(3)

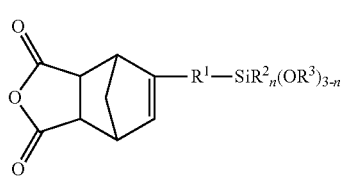
(4)

In the aforementioned formulae (1) to (4), $R^1$ represents a substituted or non-substituted, saturated divalent hydrocarbon group having 3 to 12 carbon atoms, or a substituted or non-substituted divalent hydrocarbon group having 3 to 12 carbon atoms and having an unsaturated carbon-carbon double bond or triple bond. $R^1$ is preferably linear, but may be branched. When $R^1$ is branched, no aliphatic unsaturated carbon-carbon bond is contained at the terminal of the molecular chain of the branched chain. In addition, when $R^1$ has a substituent, no aliphatic unsaturated carbon-carbon bond is contained at the terminal of the molecular chain of the substituent. As examples of $R^1$, mention may be made of an alkylene group having 3 to 12 carbon atoms, a substituted alkylene group which has a phenyl group and/or a cycloalkyl group as a pendant group, an alkylene/arylene/alkylene group, an arylene/alkylene group such as a —C$_6$H$_4$—CH$_2$CH$_2$— group, and a phenylene group.

Among these, $R^1$ is preferably an alkylene group having 3 to 12 carbon atoms, and in particular, preferably a linear alkylene group having 3 to 10 carbon atoms.

As examples of $R^1$, mention may be made of

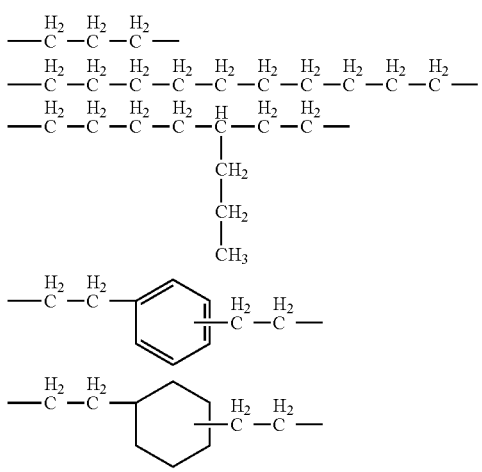

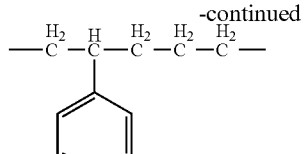

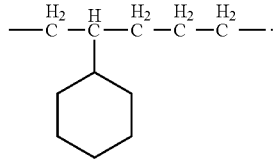

In the aforementioned formulae (1) to (4), $R^2$ is a monovalent hydrocarbon group having 1 to 10 carbon atoms and having no aliphatic unsaturated bond at the terminal of the molecular chain. As examples thereof, mention may be made of, for example, alkyl groups such as a methyl group, an ethyl group, a propyl group, a butyl group, an isobutyl group, a tertiary butyl group, a pentyl group, a cyclopentyl group, a hexyl group, a cyclohexyl group, a decyl group and the like; halogenated alkyl groups such as a 3-chloropropyl group, a 3,3,3-trifluoropropyl group and the like; as well as, aryl groups such as a phenyl group, a tolyl group, a xylyl group and the like. $R^2$ is preferably an alkyl group, and in particular, preferably a methyl group.

In the aforementioned formulae (1) to (4), $R^3$ is a monovalent hydrocarbon group having 1 to 18 carbon atoms and having no aliphatic unsaturated bond at the terminal of the molecular chain, or an alkoxyalkyl group having 2 to 18 carbon atoms. As examples of hydrocarbon groups, mention may be made of, for example, alkyl groups such as a methyl group, an ethyl group, a propyl group, a butyl group, a decyl group, a dodecyl group, a hexadecyl group and the like. As examples of alkoxyalkyl groups, mention may be made of, for example, alkoxyalkyl groups having 2 to 10 carbon atoms such as a methoxymethyl group, a methoxyethyl group, an ethoxyethyl group, an ethoxymethyl group, a methoxypropyl group, an ethoxypropyl group, a propoxypropyl group and the like. $R^3$ is preferably an alkyl group, and in particular, preferably an ethyl group or a methyl group.

In the aforementioned formulae (1) and (3), $R^4$ is a substituted or non-substituted, saturated divalent hydrocarbon group having 1 to 12 carbon atoms, or a substituted or non-substituted divalent hydrocarbon group having 2 to 12 carbon atoms and having an unsaturated carbon-carbon double bond or triple bond. The aforementioned divalent hydrocarbon group is preferably linear, but may be branched, with the proviso that the aforementioned divalent hydrocarbon group has no aliphatic unsaturated bond at the terminal of the molecular chain of the branched chain or at the terminal of the molecular chain of the substituent.

As examples of $R^4$, mention may be made of an alkylene group having 1 to 12 carbon atoms such as chain —CH$_2$—, —CH$_2$CH$_2$CH$_2$CH$_2$CH$_2$CH$_2$CH$_2$CH$_2$CH$_2$CH$_2$CH$_2$CH$_2$—, —CH(CH$_3$)—CH$_2$— and the like; a substituted alkylene group having 8 to 21 carbon atoms having a phenyl group or a cycloalkyl group as a pendant group; an alkylene/arylene/alkylene group having 8 to 21 carbon atoms such as —CH$_2$CH$_2$—C$_6$H$_4$—CH$_2$CH$_2$— and the like; an arylene/alkylene group having 8 to 21 carbon atoms such as —C$_6$H$_4$—CH$_2$CH$_2$— and the like; and a phenylene group. Among these, $R^4$ is preferably an alkylene group having 1 to 12 carbon atoms, and more preferably a linear alkylene group having 2 to 9 carbon atoms.

As examples of $R^4$, mention may be made of

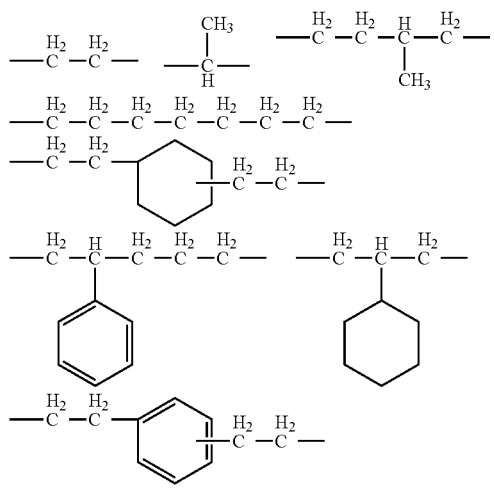

In the aforementioned formulae (1) and (3), each $R^5$ is independently a monovalent hydrocarbon group having 1 to 10 carbon atoms and having no aliphatic unsaturated bond at the terminal of the molecular chain. As examples thereof, mention may be made of, for example, alkyl groups such as a methyl group, an ethyl group, a propyl group, a butyl group, an isobutyl group, a tertiary butyl group, a pentyl group, a cyclopentyl group, a hexyl group, a cyclohexyl group, a decyl group and the like; halogenated alkyl groups such as a 3-chloropropyl group, a 3,3,3-trifluoropropyl group and the like; as well as, aryl groups such as a phenyl group, a tolyl group, a xylyl group and the like. Each $R^5$ is independently preferably selected from the group consisting of an alkyl group and a phenyl group, and in particular, preferably selected from the group consisting of a methyl group, an ethyl group, a cyclohexyl group and a phenyl group. A methyl group is most preferred. As examples of $-Si(R^5)(R^5)-$, mention may be made of the following structures:

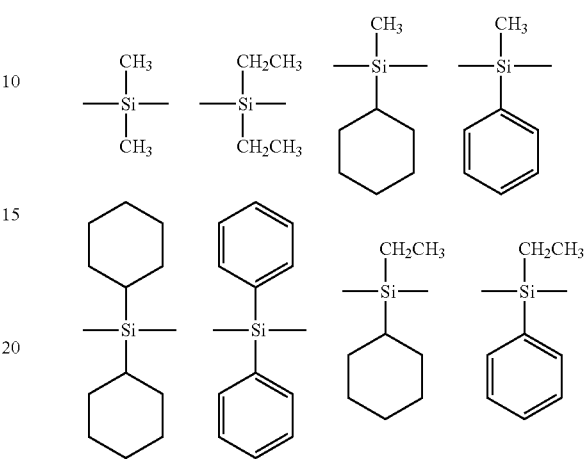

In the aforementioned formulae (1) to (4), n is 0, 1 or 2, and in particular, preferably 0 or 1.

In the aforementioned formulae (1) and (3), m is an integer ranging from 0 to 20, preferably an integer ranging from 0 to 10, more preferably an integer ranging from 0 to 2, and in particular, preferably 1 or 2.

As examples of the aforementioned novel succinic anhydride-functional organosilicon compounds represented by the aforementioned formula (1), the following compounds can be mentioned.

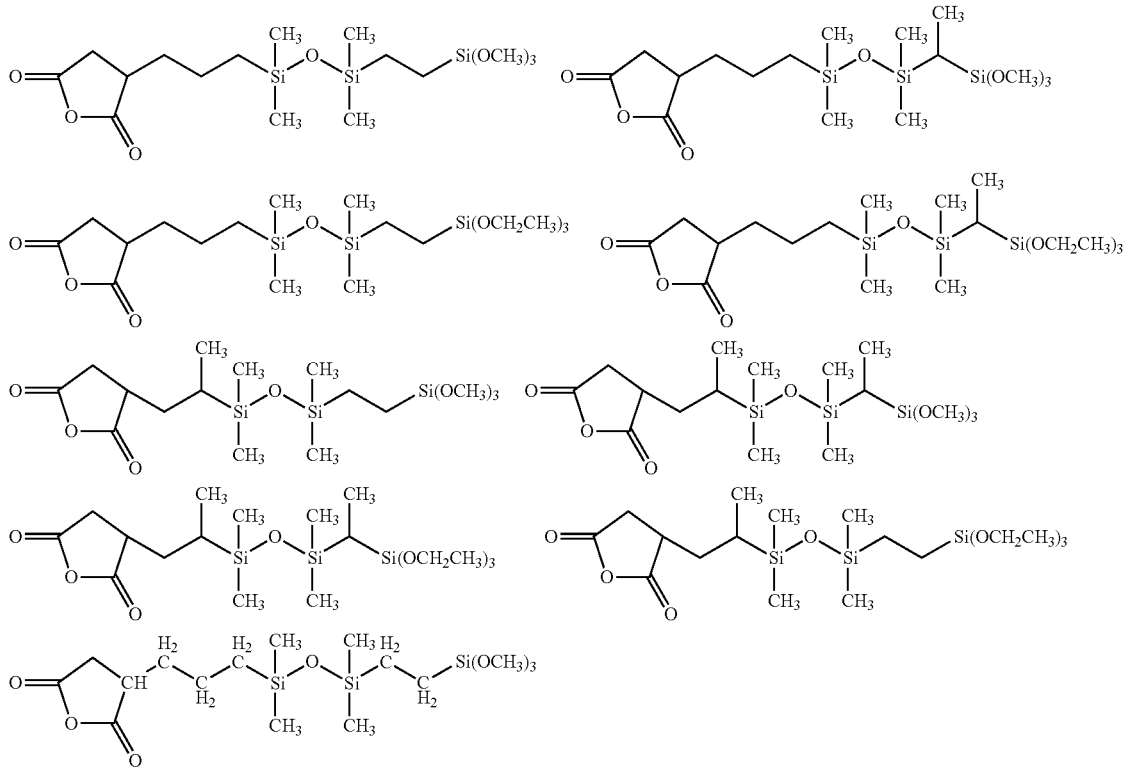

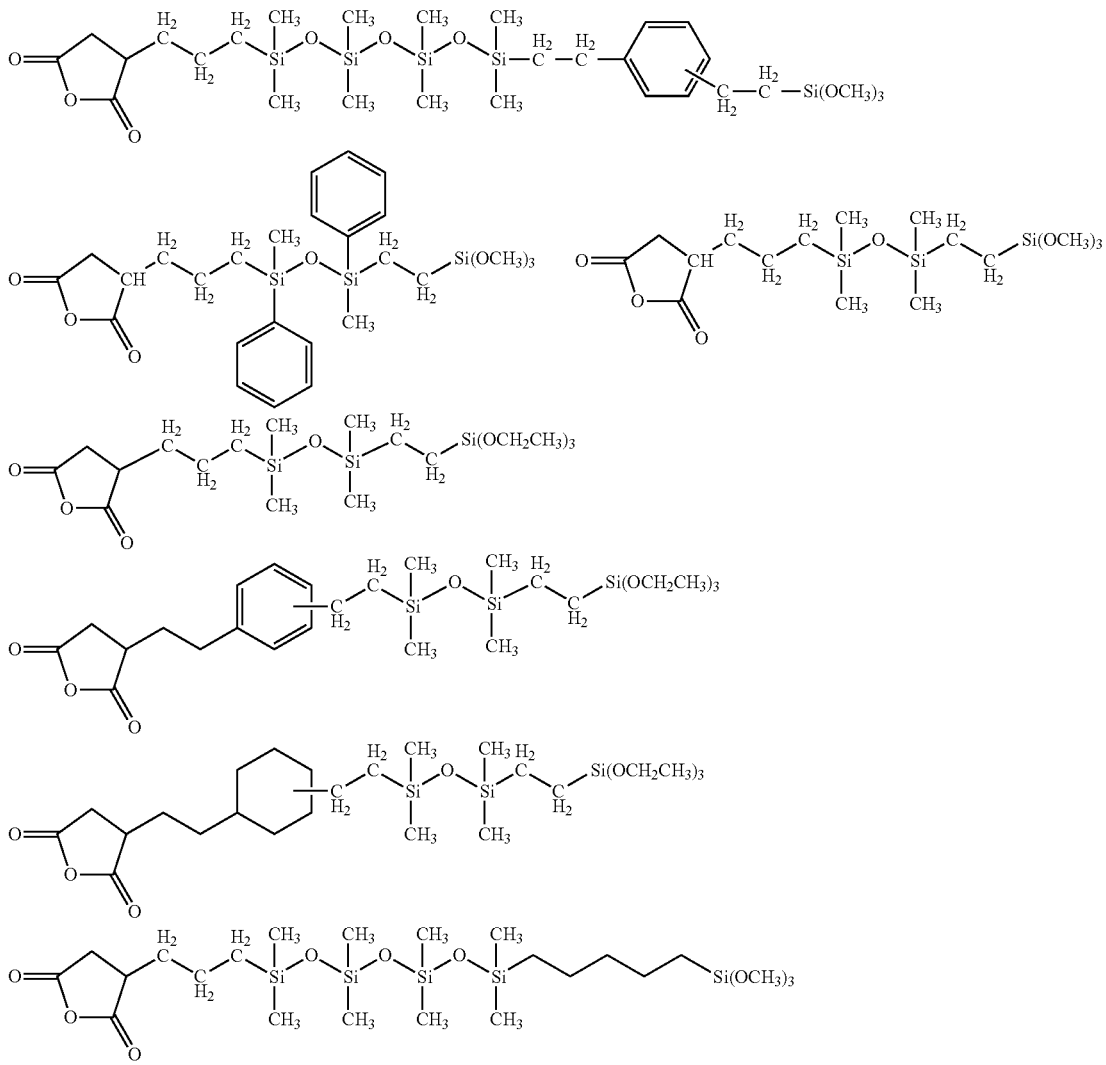

Among these, the following compounds are particularly preferred, since a high-purity product can be easily produced by distillation, and raw materials are easily commercially available.

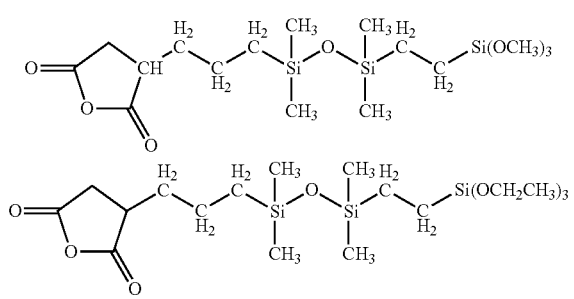

The novel compound represented by the aforementioned formula (1) can be produced by reacting an alkenyl-functional succinic anhydride represented by the following general formula (5):

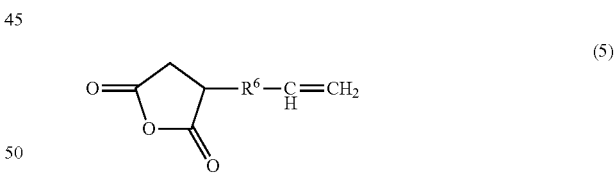

and an organosilicon compound represented by the following general formula (6):

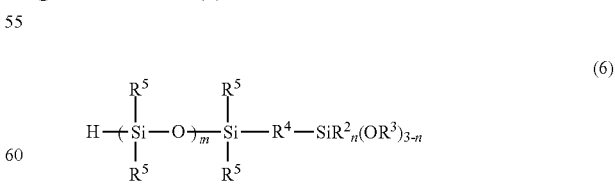

In the aforementioned formula (5), $R^6$ is a substituted or non-substituted divalent hydrocarbon group having 1 to 10 carbon atoms, and may be a substituted or non-substituted divalent hydrocarbon group having 2 to 10 carbon atoms and having an unsaturated carbon-carbon double bond. The aforementioned divalent hydrocarbon group is preferably linear, but may be branched, with the provisos that when the aforementioned divalent hydrocarbon group is a branched chain, no aliphatic unsaturated bond is present at the terminal of the molecular chain of the branched chain; and that when the aforementioned divalent hydrocarbon group has a substituent, no aliphatic unsaturated bond is present at the terminal of the molecular chain of the substituent. $R^6$ is in particular, preferably an alkylene group having 1 to 8 carbon atoms. In the aforementioned formula (6), $R^2$, $R^3$, $R^4$, $R^5$, m and n are the same as defined above in the aforementioned formula (1).

Since $R^3$ in the aforementioned formulae (1) to (4) is a monovalent hydrocarbon group or an alkoxyalkyl group, and in particular, preferably an alkyl group or an alkoxyalkyl group, as described above, the compounds of the aforementioned formulae (1) to (4) and (6) are alkoxysilyl-functional organosilicon compounds or alkoxyalkoxysilyl-functional organosilicon compounds.

The organosilicon compound represented by the aforementioned formula (6) can be easily produced by means of a hydrosilylation reaction between a diorganosiloxane oligomer of which both terminals of the molecular chain are capped with diorganohydrogensilyl groups and an alkenyl group-containing alkoxysilane and/or alkenyl group-containing alkoxyalkoxysilane. The molar ratio of the diorganosiloxane oligomer of which both terminals of the molecular chain are capped with diorganohydrogensilyl groups to the alkenyl group-containing alkoxysilane and/or alkenyl group-containing alkoxyalkoxysilane preferably ranges from 0.8:1.0 to 1.2:1.0.

In the case of reacting an alkenyl-functional succinic anhydride (5) and an organosilicon compound (6), the organosilicon compound (6) is preferably used in an amount ranging from 1.0 to 10.0 mol and more preferably used in an amount ranging from 1.0 to 1.5 mol, with respect to one mol of the alkenyl-functional succinic anhydride (5). By using one or more mol of the organosilicon compound (6) with respect to one mol of the alkenyl-functional succinic anhydride (5), prevention of a large amount of unreacted alkenyl-functional succinic anhydride (5) remaining is possible, and a yield of an objective product can be increased. On the other hand, by using 10.0 mol or less of the organosilicon compound (6) with respect to one mol of the alkenyl-functional succinic anhydride (5), reduction of a pot yield in the production which is caused by a large amount of the organosilicon compound (6) remaining can be controlled, and this is economically advantageous.

As a method for introducing the alkenyl-functional succinic anhydride (5) and the organosilicon compound (6) in a reactor, any method can be used. The mixing molar ratio of the aforementioned compounds is preferably present within the aforementioned range. In addition, the organosilicon compound (6) may be introduced in the alkenyl-functional succinic anhydride (5) under heating conditions, or vice versa may be applied. The temperature in the case of carrying out the reaction under heating is preferably within a preferable range of the reaction temperature described below.

The temperature of the reaction between the alkenyl-functional succinic anhydride (5) and the organosilicon compound (6) is not particularly restricted, as long as the objective reaction can proceed. The aforementioned reaction can be carried out in any temperature and may be carried out under heating. In this case, the reaction temperature preferably ranges from 100° C. to 180° C. By specifying the reaction temperature to 100° C. or higher, the reaction rate is increased and the reaction period for producing the desirable product can be shortened. Therefore, this is economically advantageous. On the other hand, by specifying the reaction temperature to 180° C. or lower, the possibility of coloration of the product can be reduced.

The aforementioned reaction can be carried out under any pressure, and in particular, there is no restriction of pressure. In the case of failing to reach the desirable temperature at the time of heating under normal pressure or in the case of taking a remarkably long time to complete the reaction under normal pressure, depending on the boiling points of raw materials used, the reaction may be carried out under exerting pressure. In this case, any pressure can be used, but preferably ranges from 1 kPa to 5 kPa. By carrying out the aforementioned reaction under 1 kpa or more, it is difficult for reduction of yield of the target product to occur.

The aforementioned reaction is preferably carried out under an atmosphere of inert gas such as nitrogen or argon. In addition, the moisture content of the alkenyl-functional succinic anhydride (5) and the organosilicon compound (6) is preferably reduced as small as possible.

In addition, in the aforementioned reaction, an organic solvent containing no active hydrogen, selected from, for example, toluene, xylene, benzene, hexane, ethylene chloride, chloroform, trichloroethylene, and cyclohexane may be used, if necessary. When the aforementioned reaction is carried out with a low polar solvent, the reaction efficacy may be reduced in some cases. For this reason, use of none of the aforementioned organic solvents is generally preferable.

The catalyst for use in the hydrosilylation reaction between the compound of the aforementioned formula (5) and the compound of the aforementioned formula (6) is a catalyst for accelerating the reaction of adding the silicon-bonded hydrogen atom in the aforementioned formula (6) (namely, a hydrogen atom bonding to a silicon atom) to the alkenyl group in the aforementioned formula (5). As examples thereof, mention may be made of, for example, a catalyst based on a VIII transition metal in the long format of the Periodic Table. A platinum-based catalyst is preferred. As examples of the aforementioned platinum-based catalyst, mention may be made of chloroplatinic acid, an alcohol solution of chloroplatinic acid, a platinum-olefin complex, a platinum-alkenylsiloxane complex, and a platinum-carbonyl complex. The catalytic amount used is not particularly restricted as long as the objective reaction can proceed.

On the other hand, the compound represented by the aforementioned formula (2) can be obtained by means of a hydrosilylation reaction between the alkenyl-functional succinic anhydride represented by the aforementioned formula (5) and a hydrosilane represented by the following general formula (7):

$$HSiR^2{}_n(OR^3)_{3-n} \qquad (7).$$

The same molar ratio of the raw materials used, the reaction temperature, reaction pressure, reaction atmosphere, and reaction solvent of hydrosilylation, as well as the hydrosilylation catalyst as described in the aforementioned hydrosilylation reaction for producing the compound of the aforementioned formula (1) using the compound of the aforementioned formula (5) and the compound of the aforementioned formula (6) can be applied as they are, in the hydrosilylation reaction between the compound of the aforementioned formula (5) and the compound of the aforementioned formula (7).

As examples of compounds represented by formula (2), mention may be made of an acid anhydride represented by the following formula:

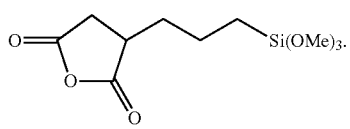

In the curable silicone composition of the present invention, as other optional components, an inorganic filler may be added. As examples of the aforementioned inorganic fillers, mention may be made of silica-based fine powders such as fumed silica, precipitated silica, pyrogenic silica, pulverized quartz and the like; metal oxide fine powders such as titanium oxide, aluminum oxide, iron oxide and the like; metal hydroxide fine powders such as aluminum hydroxide, magnesium hydroxide and the like; fine powders obtained by surface-treating the aforementioned inorganic fillers with a compound selected from organic silicon compounds such as organoalkoxysilane, organohalosilane, organosilazane and the like.

The amount of the aforementioned inorganic filler in the composition of the present invention is not particularly restricted. In order to improve mechanical strength of the obtained cured product, the amount of the inorganic filler preferably ranges from 1 to 100 parts by mass and more preferably ranges from 1 to 50 parts by mass, with respect to 100 parts by mass of the aforementioned component (A).

In addition, as the adhesion promoter in order to improve adhesive properties of the composition of the present invention, an organotrialkoxysilane (component E), and in particular, an organotrialkoxysilane selected from the group consisting of vinyltrimethoxysilane, allyltrimethoxysilane, 3-methacryloxypropyltrimethoxysilane, 3-glycidoxypropyltrimethoxysilane, 3-aminopropyltrimethoxysilane, N-(2-aminoethyl)-3-aminopropyltrimethoxysilane and the like may be added to the composition of the present invention. The amount of the aforementioned adhesion promoter contained in the composition of the present invention is not particularly restricted. The amount preferably ranges from 0.01 to 10 parts by mass with respect to 100 parts by mass of the aforementioned component (A).

In addition, in order to adjust the curing rate of the composition of the present invention and improve workability, a curing controlling agent selected from an acetylene-based compound such as 2-methyl-3-butyn-2-ol, 3,5-dimethyl-1-hexyn-3-ol, 2-phenyl-3-butyn-2-ol and the like; an enyne compound such as 3-methyl-3-penten-1-yne, 3,5-dimethyl-3-hexen-1-yne and the like; 1,3,5,7-tetramethyl-1,3,5,7-tetravinylcyclotetrasiloxane, 1,3,5,7-tetramethyl-1,3,5,7-tetrahexenylcyclotetrasiloxane; a triazole such as benzotriazole; a phosphine, a mercaptan, a hydrazine and the like are preferably contained in the composition of the present invention. The amount of the aforementioned curing controlling agent is not particularly restricted, and preferably ranges from 0.001 to 5 parts by mass with respect to 100 parts by mass of the aforementioned component (A).

In addition, in the composition of the present invention, additives selected from the group consisting of known pigments, thermal resistance agents, flame retardants and the like may be optionally contained, as long as the purposes of the present invention are not impaired.

The method for preparing the composition of the present invention is not particularly restricted. Component (A) to component (D), and, if desired, component (E) and other optional components are mixed, and thereby, the composition of the present invention can be produced. In the case of containing the inorganic filler in the composition of the present invention, component (B) to component (D) are preferably added to a base compound previously prepared by heating and mixing component (A) and the inorganic filler. When the aforementioned base compound is prepared, the aforementioned organosilicon compound is added and the surface of the inorganic filler may be subjected to an in-situ treatment. When the composition of the present invention is prepared, a known kneading apparatus such as a twin-roll, a kneader mixer, a ross mixer and the like can be used.

The aforementioned curable silicone compositions of the present invention exhibit superior fluidity and filling properties. The viscosity thereof is not particularly restricted, and in general, preferably ranges from 100 to 500,000 mPa·s, and in particular, ranges from 100 to 100,000 mPa·s at 25° C.

EXAMPLES

The curable silicone compositions of the present invention are described in detail on the basis of examples. The viscosity in the Examples is a value measured at 25° C. In the following formulae, Me stands for a methyl group and Vi stands for a vinyl group. In addition, evaluation of adhesive properties with respect to PPS (polyphenylene sulfide) was carried out as follows.

Adhesive Properties with Respect to PPS

The adhesive properties of the curable silicone compositions were measured in accordance with a test method for tensile shear adhesive strength specified in JIS K 6850.

Namely, a PPS adherend with a size of 100 mm×20 mm×1.6 mm and an aluminum adherend with a size of 100 mm×20 mm×1.6 mm were used, and an adhesive layer composed of a curable silicone composition was formed between those adherends so that the size of the adhesive layer was 10 mm×20 mm×1 mm, followed by heating at 120° C. for a specified period (for 30 minutes or for 60 minutes) to cure the aforementioned composition. Thereby, a test piece was prepared. The tensile shear adhesive strength of the aforementioned test piece was measured with a rate of pulling of 50 mm/minutes. The condition of the adhesive interface of the PPS adherend after the measurement was observed. The rate of cohesive failure of the silicone cured product was indicated by a CF index (index of cohesive failure). The case in which the CF index was 0% was indicated by AF (adhesive failure). In addition, by way of comparison, an adhesive layer composed of a curable silicone composition was formed between aluminum adherends with a size of 100 mm×20 mm×1.6 mm so that the size of the adhesive layer was 10 mm×20 mm×1 mm, followed by heating at 120° C. for a specified period (for 30 minutes or for 60 minutes) to cure the aforementioned composition. Thereby, a test piece was prepared. In the same manner as described above, the tensile shear adhesive strength thereof was measured, and the adhesive interface of the aluminum adherend after the measurement was observed. The rate of cohesive failure of the silicone cured product was indicated by a CF index (index of cohesive failure).

Example 1

14.01 g (0.1 mol) of allylsuccinic anhydride (manufactured by Wako Pure Chemical Industries, Ltd.) and a platinum-1,3-divinyl-1,1,3,3-tetramethyldisiloxane complex, in an amount such that the amount of the platinum metal in the complex was 15 ppm with respect to the amount of allylsuccinic anhydride, were placed in a four-necked flask with a volume of 50 mL, equipped with an inlet tube for nitrogen gas, a thermometer, a Dimroth condenser and a dropping funnel, and the mixture was heated to 100° C. and stirred.

Subsequently, 28.26 g (0.1 mol) of 1-hydrogen-3-(2'-trimethoxysilylethyl)-1,1,3,3-tetramethyldisiloxane was added dropwise to the reaction mixture over one hour. Since the reaction was an exothermic reaction, the reaction was carried out while the flask was appropriately cooled. After completion of the dropwise addition of hydrogensiloxane, the mixture was further stirred at 110° C. for one hour to complete the reaction. Subsequently, the reaction mixture was distilled under reduced pressure. Thereby, the main fraction of distillate having a boiling point ranging from 211 to 213° C./1 torr) was obtained in an amount of 32.40 g (yield=76.7 mass %). From the results of nuclear magnetic resonance spectral analysis and gas chromatograph mass analysis, it could be confirmed that the aforementioned product was an acid anhydride represented by the following formula:

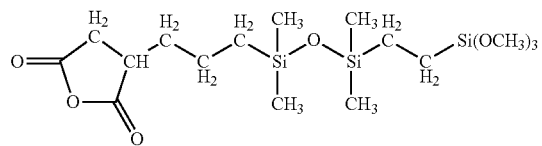

The following is a result of analysis by means of $^{13}$C NMR spectra of the aforementioned product.

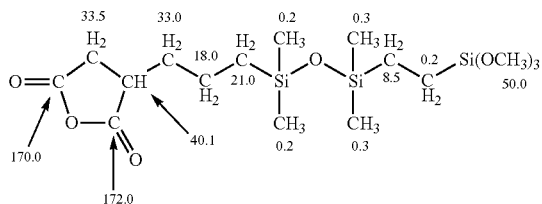

[13C NMR] (Numbers mean chemical shift values (ppm))

Example 2

A hydrosilylation reaction between allylsuccinic anhydride and a hydrosilane compound was carried out in the same manner as described in Example 1, with the exception of using 1-hydrogen-3-(1'-trimethoxysilyl-1'-methyl-methyl)-1,1,3,3-tetramethyldisiloxane instead of 1-hydrogen-3-(2'-trimethoxysilylethyl)-1,1,3,3-tetramethyldisiloxane. The reaction mixture was distilled under reduced pressure. Thereby, the main fraction of distillate having a boiling point ranging from 201 to 203° C./1 torr) was obtained in an amount of 28.1 g (yield=66.5 mass %). From the results of nuclear magnetic resonance spectral analysis and gas chromatograph mass analysis, it could be confirmed that the aforementioned product was an acid anhydride represented by the following formula:

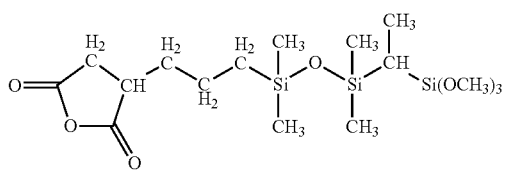

The following is a result of analysis by means of $^{13}$C NMR spectra of the aforementioned product.

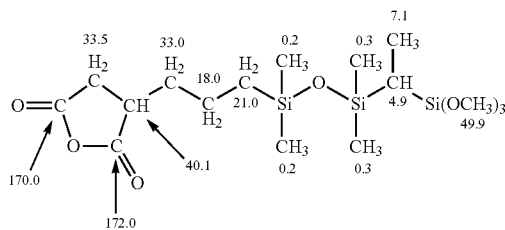

[$^{13}$C NMR] (Numbers mean chemical shift values (ppm))

Example 3

20.4 g (0.10 mol) of 5-hexenyltrimethoxysilane (manufactured by Dow Corning Toray Co., Ltd.), 9.80 g (0.10 mol) of maleic anhydride (manufactured by Wako Pure Chemical Industries, Ltd.) and 2.0×10$^{-3}$ g (67 ppm) of phenothiazine (manufactured by Wako Pure Chemical Industries, Ltd.), were placed in a four-necked flask with a volume of 50 mL, a thermometer, a stirrer and a Dimroth condenser, and the mixture was heated between 150° C. and 160° C. and stirred for 48 hours under normal pressure. Subsequently, the reaction mixture was distilled under reduced pressure. Thereby, the colorless and transparent liquid having a boiling point ranging from 149 to 151° C./1 torr) was obtained in an amount of 21.4 g. From the results of nuclear magnetic resonance spectral analysis and gas chromatograph mass analysis, it could be confirmed that the aforementioned product was dihydroro-3-[6-(trimethoxysilyl)-2-hexen-1-yl]-2,5-furandione represented by the following formula:

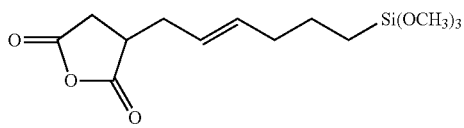

The following numbers mean chemical shifts value and assignments by means of $^{13}$C NMR spectra and $^{29}$Si NMR spectra of the aforementioned product.

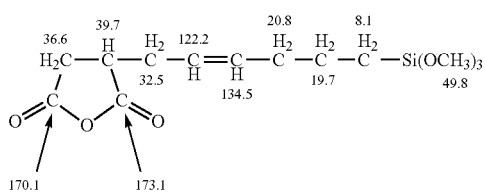

[$^{13}$C-NMR]
(Numbers mean chemical shift values of each carbon atom (ppm))

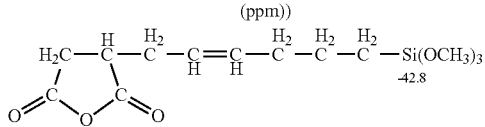

[$^{29}$Si-NMR] (Numbers mean chemical shift values (ppm))

Example 4

A curable silicone composition was produced by uniformly mixing 50 parts by mass of a dimethylpolysiloxane having both terminals of the molecular chain capped with dimethylvinylsiloxy groups, with a viscosity of 50 Pa·s, 10 parts by mass of a resin organopolysiloxane represented by the average unit formula: $[(CH_2{=}CH)(CH_3)_2SiO_{1/2}]_{0.07}$ $[(CH_3)_3SiO_{1/2}]_{0.71}$ $(SiO_{4/2})_{1.00}$, having a masa average molecular weight of 20,000 calculated on the basis of a polystyrene standard, measured by gel permeation chromatography, 3 parts by mass of a copolymer of methylhydrogensiloxane and dimethylsiloxane with both terminals capped with trimethylsiloxy groups, having a viscosity of 40 mPa·s (the amount of the silicon-bonded hydrogen atom in the copolymer was 2.9 mol with respect to one mol of the total of the vinyl groups in the aforementioned dimethylpolysiloxane and resin organopolysiloxane), 40 parts by mass of crystalline silica fine powder (MIN-U-SIL (trademark) 5, manufactured by U.S. Silica Company), 1.2 parts by mass of 3-glycidoxypropyltrimethoxysilane, 1 part by mass of an acid anhydride represented by the following formula:

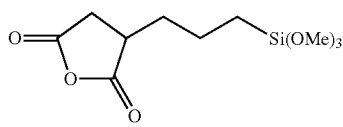

2-phenyl-3-butyn-2-ol as a reaction controlling agent (in an amount of 1,000 ppm on the basis of a mass unit in the composition of the present invention), and a platinum-based catalyst (in an amount of 8 ppm of the platinum atom on the basis of a mass unit with respect to the composition of the present invention). The evaluation results of adhesive properties of the obtained curable silicone composition with respect to PPS are shown in Table 1.

Example 5

A curable silicone composition was produced in the same manner as described in Example 4, with the exception of using the acid anhydride prepared in Example 1 instead of the acid anhydride used in Example 4, in the same amount as the acid anhydride used in Example 4. The evaluation results of adhesive properties of the obtained curable silicone composition with respect to PPS are shown in Table 1.

Example 6

A curable silicone composition was produced in the same manner as described in Example 4, with the exception of using the acid anhydride prepared in Example 2 instead of the acid anhydride used in Example 4, in the same amount as the acid anhydride used in Example 4. The evaluation results of adhesive properties of the obtained curable silicone composition with respect to PPS are shown in Table 1.

Comparative Example 1

A curable silicone composition was produced in the same manner as described in Example 4, with the exception of using allylsuccinic anhydride instead of the acid anhydride used in Example 4, in the same amount as the acid anhydride used in Example 4. The evaluation results of adhesive properties of the obtained curable silicone composition with respect to PPS are shown in Table 1.

Comparative Example 2

A curable silicone composition was produced in the same manner as described in Example 4, with the exception of using no acid anhydride. The evaluation results of adhesive properties of the obtained curable silicone composition with respect to PPS are shown in Table 1.

TABLE 1

| Curing period | Adherend | Measurement item | Example 4 | Example 5 | Example 6 | Comparative Example 1 | Comparative Example 2 |
|---|---|---|---|---|---|---|---|
| 30 min. | Aluminum (Al)/PPS | Cohesive failure index (%) | 70 | 100 | 100 | AF | AF |
| | | Shear adhesive strength (MPa) | 2.6 | 3.1 | 3.1 | 1.4 | 1.3 |
| | Al/Al | Cohesive failure index (%) | 100 | 100 | 100 | 100 | 100 |
| | | Shear adhesive strength (MPa) | 3.2 | 3.2 | 3.2 | 1.9 | 3.2 |
| 60 min. | Al/PPS | Cohesive failure index (%) | 100 | 100 | 100 | 10 | 40 |
| | | Shear adhesive strength (MPa) | 3.1 | 3.2 | 3.2 | 1.5 | 2.6 |
| | Al/Al | Cohesive failure index (%) | 100 | 100 | 100 | 100 | 100 |
| | | Shear adhesive strength (MPa) | 3.2 | 3.2 | 3.2 | 1.9 | 3.2 |

INDUSTRIAL APPLICABILITY

The succinic anhydride-functional organosilicon compound of the present invention is useful as an additive for organic resins such as a silane coupling agent, a coating agent, a surface-treating agent for an inorganic material, a fiber-treating agent, an adhesion promoter and the like, or a denaturing agent for polymers. In particular, the succinic anhydride-functional organosilicon compound is useful as an adhesion promoter for an addition reaction-curable silicone composition or a condensation reaction-curable silicone composition.

The curable silicone compositions of the present invention possess good adhesive properties with respect to a poor adhesive resin such as PPS and the like, even in the case of curing at a relatively low temperature. For this reason, the curable silicone compositions of the present invention are suitable as a sealing agent or an adhesive for electronic parts in vehicles such as ECU (electronic control units) and the like in which poor-adhesive resins such as PPS and the like are used.

The invention claimed is:

1. An organosilicon compound represented by the following general formula (I):

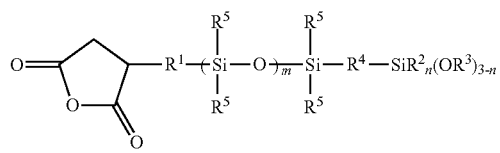

(I)

wherein
- $R^1$ represents a substituted or non-substituted, saturated divalent hydrocarbon group having 3 to 12 carbon atoms, or a substituted or non-substituted divalent hydrocarbon group having 3 to 12 carbon atoms and having an unsaturated carbon-carbon double bond or triple bond, with the provisos that when $R^1$ is a branched chain, no aliphatic unsaturated carbon-carbon bond is contained at the terminal of the molecular chain of the branched chain, and that when $R^1$ has a substituent, no aliphatic unsaturated carbon-carbon bond is contained at the terminal of the molecular chain of the substituent;
- $R^2$ is a monovalent hydrocarbon group having 1 to 10 carbon atoms and having no aliphatic unsaturated bond at the terminal of the molecular chain;
- $R^3$ is a monovalent hydrocarbon group having 1 to 18 carbon atoms and having no aliphatic unsaturated bond at the terminal of the molecular chain, or an alkoxyalkyl group having 2 to 18 carbon atoms;
- $R^4$ is a substituted or non-substituted divalent hydrocarbon group having 1 to 12 carbon atoms, with the provisos that when $R^4$ is a branched chain, no aliphatic unsaturated carbon-carbon bond is contained at the terminal of the molecular chain of the branched chain, and that when $R^4$ has a substituent, no aliphatic unsaturated carbon-carbon bond is contained at the terminal of the molecular chain of the substituent;
- each $R^5$ is independently a monovalent hydrocarbon group having 1 to 10 carbon atoms and having no aliphatic unsaturated bond at the terminal of the molecular chain;
- m is an integer ranging from 1 to 20; and
- n is 0, 1 or 2.

2. A method for producing the organosilicon compound according to claim 1, the method comprising reacting an alkenyl-functional succinic anhydride represented by the following general formula (II):

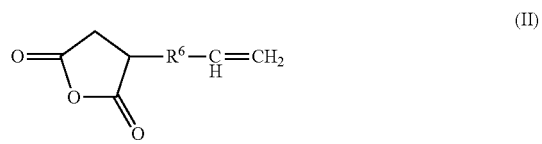

(II)

wherein
- $R^6$ is a substituted or non-substituted divalent hydrocarbon group having 1 to 10 carbon atoms; and an organosilicon compound represented by the following general formula (III):

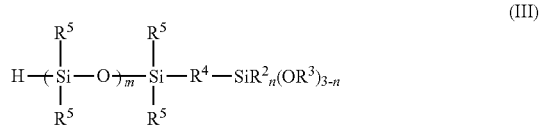

(III)

wherein
- $R^2$, $R^3$, $R^4$, $R^5$, m and n are the same as defined above in the general formula (I), in the presence of a hydrosilylation reaction-catalyst.

3. A curable silicone composition comprising the organosilicon compound according to claim 1 as an adhesion promoter.

4. A method for producing a succinic anhydride-functional organosilicon compound, the method comprising reacting an alkenyl-functional organosilicon compound and maleic anhydride, wherein the alkenyl-functional organosilicon compound has a silicon-bonded group that contains a structure: $H_2C=CH-CH_2-$ at the terminal of the molecular chain, or a silicon-bonded 2-propenyl group.

5. A method for producing a succinic anhydride-functional organosilicon compound represented by the following general formula (IV):

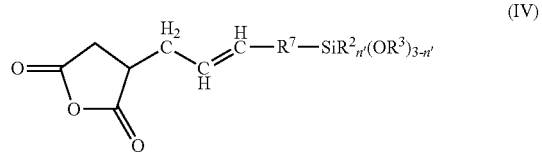

(IV)

wherein
- $R^2$ is a monovalent hydrocarbon group having 1 to 10 carbon atoms and having no aliphatic unsaturated bond at the terminal of the molecular chain;
- $R^3$ is a monovalent hydrocarbon group having 1 to 18 carbon atoms and having no aliphatic unsaturated bond at the terminal of the molecular chain, or an alkoxyalkyl group having 2 to 18 carbon atoms;
- $R^7$ represents a single bond directly bonding between $-CH_2-$ at the left of $R^7$ and Si atom at the right of $R^7$; a saturated divalent hydrocarbon group having 1 to 21 carbon atoms, or a substituted or non-substituted divalent hydrocarbon group having 2 to 21 carbon atoms and having an unsaturated carbon-carbon double bond or triple bond, with the provisos that when $R^7$ is a branched chain, no aliphatic unsaturated carbon-carbon bond is contained at the terminal of the molecular chain of the branched chain, and that when $R^7$ has a substituent, no aliphatic unsaturated carbon-carbon bond is contained at the terminal of the molecular chain of the substituent; or a group represented by the following formula:

$$-R^8-(Si(R^{10})_2O)_a-R^9-$$

wherein each $R^8$ and $R^9$ is independently a substituted or non-substituted saturated divalent hydrocarbon group having 1 to 15 carbon atoms, or a substituted or non-substituted divalent hydrocarbon group having 2 to 15 carbon atoms and having an unsaturated carbon-carbon double bond or triple bond, with the provisos that when the divalent hydrocarbon group is a branched chain, no aliphatic unsaturated carbon-carbon bond is contained at the terminal of the molecular chain of the branched chain, and that when the divalent hydrocarbon group has a substituent, no aliphatic unsaturated carbon-carbon bond is contained at the terminal of the molecular chain of the substituent;

$R^{10}$ is a monovalent hydrocarbon group having 1 to 10 carbon atoms and having no aliphatic unsaturated bond at the terminal of the molecular chain; and a is an integer ranging from 0 to 10; and n' is 0, 1 or 2;

the method comprising reacting an alkenyl-functional organosilicon compound represented by the following general formula (V):

$$H_2C=\underset{H}{C}-\overset{H_2}{C}-R^7-SiR^2_{n'}(OR^3)_{3-n'} \quad (V)$$

wherein $R^2$, $R^3$, $R^7$ and n' are the same as defined above in the formula (IV); and a maleic anhydride represented by the following formula (VI):

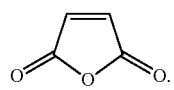 (VI)

6. The method according to claim 5, wherein a temperature for the reaction between the alkenyl-functional organosilicon compound and maleic anhydride is in the range of 100° C. to 180° C.

7. The method according to claim 5, wherein the alkenyl-functional organosilicon compound is used in amount ranging from 1 to 10 mol with respect to one mol of the maleic anhydride.

8. A curable silicone composition comprising:
(A) an organopolysiloxane having at least two alkenyl groups in a molecule, in an amount of 100 parts by mass;
(B) an organopolysiloxane having at least two silicon-bonded hydrogen atoms in a molecule, in an amount in which an amount of the silicon-bonded hydrogen atom in said component (B) ranges from 0.1 to 10 mol with respect to 1 mol of the alkenyl group of said component (A);
(C) a hydrosilylation-reaction catalyst, in a catalytic amount; and
(D) an acid anhydride represented by the following general formula (1):

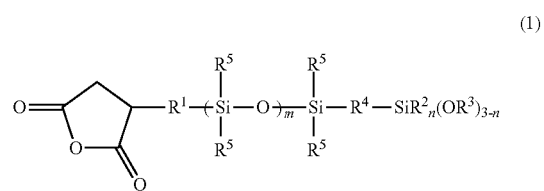 (1)

wherein $R^1$ represents a substituted or non-substituted, saturated divalent hydrocarbon group having 3 to 12 carbon atoms, or a substituted or non-substituted divalent hydrocarbon group having 3 to 12 carbon atoms and having an unsaturated carbon-carbon double bond or triple bond, with the provisos that when $R^1$ is a branched chain, no aliphatic unsaturated carbon-carbon bond is contained at the terminal of the molecular chain of the branched chain, and that when $R^1$ has a substituent, no aliphatic unsaturated carbon-carbon bond is contained at the terminal of the molecular chain of the substituent;

$R^2$ is a monovalent hydrocarbon group having 1 to 10 carbon atoms and having no aliphatic unsaturated bond at the terminal of the molecular chain;

$R^3$ is a monovalent hydrocarbon group having 1 to 18 carbon atoms and having no aliphatic unsaturated bond at the terminal of the molecular chain, or an alkoxyalkyl group having 2 to 18 carbon atoms;

$R^4$ is a substituted or non-substituted divalent hydrocarbon group having 1 to 12 carbon atoms, with the provisos that when $R^4$ is a branched chain, no aliphatic unsaturated carbon-carbon bond is contained at the terminal of the molecular chain of the branched chain, and that when $R^4$ has a substituent, no aliphatic unsaturated carbon-carbon bond is contained at the terminal of the molecular chain of the substituent;

each $R^5$ is independently a monovalent hydrocarbon group having 1 to 10 carbon atoms and having no aliphatic unsaturated bond at the terminal of the molecular chain;

m is an integer ranging from 1 to 20; and n is 0, 1 or 2, in an amount ranging from 0.1 to 20 parts by mass.

9. The curable silicone composition according to claim 8, wherein said component (A) is a mixture of (A1) a linear organopolysiloxane having at least two alkenyl groups in a molecule and (A2) a branched organopolysiloxane having at least two alkenyl groups in a molecule.

10. The curable silicone composition according to claim 8, further comprising (E) an organotrialkoxysilane.

11. The method according to claim 6, wherein the alkenyl-functional organosilicon compound is used in amount ranging from 1 to 10 mol with respect to one mol of the maleic anhydride.

* * * * *